United States Patent
Wang et al.

(10) Patent No.: US 11,524,961 B2
(45) Date of Patent: Dec. 13, 2022

(54) JAK KINASE INHIBITOR AND PREPARATION METHOD AND USE THEREOF

(71) Applicant: Shanghai Longwood Biopharmaceuticals Co., Ltd., Shanghai (CN)

(72) Inventors: Zhe Wang, Shanghai (CN); Guoqin Fan, Shanghai (CN); Sai Yang, Shanghai (CN); Zhihong Zeng, Shanghai (CN)

(73) Assignee: SHANGHAI LONGWOOD BIOPHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 16/480,174

(22) PCT Filed: Jan. 23, 2018

(86) PCT No.: PCT/CN2018/073776
§ 371 (c)(1),
(2) Date: Jul. 23, 2019

(87) PCT Pub. No.: WO2018/133875
PCT Pub. Date: Jul. 26, 2018

(65) Prior Publication Data
US 2019/0382408 A1  Dec. 19, 2019

(30) Foreign Application Priority Data
Jan. 23, 2017  (CN) .......................... 201710058693.3

(51) Int. Cl.
*C07D 487/04* (2006.01)
(52) U.S. Cl.
CPC ................... *C07D 487/04* (2013.01)
(58) Field of Classification Search
CPC .................................................. C07D 487/04
See application file for complete search history.

(56) References Cited

U.S. PATENT DOCUMENTS

| | | |
|---|---|---|
| 2009/0233903 A1 | 9/2009 | Rodgers et al. |
| 2012/0077798 A1 | 3/2012 | Rodgers et al. |
| 2013/0225556 A1 | 8/2013 | Rodgers et al. |

FOREIGN PATENT DOCUMENTS

| | | |
|---|---|---|
| CN | 102026999 A | 4/2011 |
| CN | 106496233 B | 5/2018 |
| WO | 2009114512 A1 | 9/2009 |
| WO | 2010/039939 A1 | 4/2010 |
| WO | 2011130146 A1 | 10/2011 |
| WO | 2013/173506 A2 | 11/2013 |
| WO | 2015131031 A1 | 9/2015 |
| WO | 2016205487 A1 | 12/2016 |
| WO | 2017/097224 A1 | 6/2017 |

OTHER PUBLICATIONS

Int'l Search Report dated May 3, 2018 in Int'l Application No. PCT/CN2018/073776.
Examination Report dated Feb. 13, 2020 in IN Application No. 201927030771.
Office Action dated Nov. 4, 2020 in CA Application No. 3055233.
Examination Report dated Dec. 18, 2019 in AU Application No. 2018209579.
Supplementary European Search Report dated Jul. 23, 2020 in EP Application No. 18741513.8.

*Primary Examiner* — Brian E McDowell
(74) *Attorney, Agent, or Firm* — Panitch Schwarze Belisario & Nadel LLP

(57) ABSTRACT

Provided is a selective JAK kinase selective inhibitor and a preparation method and the use thereof. In particular, provided is a compound having the structure as shown in chemical formula (I) as a JAK kinase inhibitor or a stereoisomer or a tautomer thereof, or a pharmaceutically acceptable salt, a hydrate or a solvate thereof.

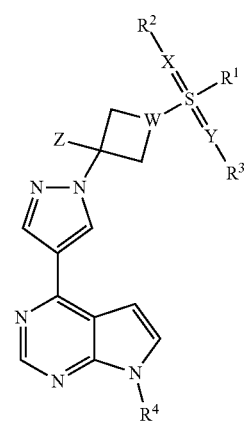

5 Claims, No Drawings

JAK KINASE INHIBITOR AND PREPARATION METHOD AND USE THEREOF

CROSS-REFERENCE TO RELATED APPLICATION

This application is a Section 371 of International Application No. PCT/CN2018/073776, filed Jan. 23, 2018, which was published in the Chinese language on Jul. 26, 2018 under International Publication No. WO 2018/133875 A1, which claims priority under 35 U.S.C. § 119(b) to Chinese Application No. 201710058693.3, filed Jan. 23, 2017, and the disclosures of which are incorporated herein by reference.

FIELD OF THE INVENTION

The present invention belongs to the field of pharmaceutical synthesis, and in particular, the present invention relates to a JAK enzyme inhibitor and the preparation method and use thereof.

BACKGROUND OF THE INVENTION

Protein kinases, also known as protein phosphokinases, are a class of enzymes that catalyze the phosphorylation of proteins, and are the key factor of regulating cellular signaling (including cell proliferation and cell differentiation).

Currently, there are four known mammal JAK family members: JAK1 (also known as Janus kinase-1). JAK2 (also known as Janus kinase-2). JAK3 (also known as JAKL or L-JAK, Janus kinase of white blood cells; and Janus kinase-3) and TYK2 (also known as protein-tyrosine kinase 2).

Blocking signal transduction at JAK kinase levels provides promise for the development of therapeutic approaches for inflammatory diseases, autoimmune diseases, myeloproliferative diseases and cancer. Inhibition of JAK kinases also contributes to the treatment of skin immune diseases such as psoriasis and skin sensitization. Commercially available medicines include Pfizer's Tofici-tinib for the treatment of rheumatoid arthritis; and Incyte's rosotinib for the treatment of myelofibrosis and acute graft-versus-host disease.

However, certain existing JAK enzyme inhibitors also have some obvious side effects. For example, some JAK inhibitors would lead to the following side effects: infections, including pneumonia, viral infections (such as herpes zoster infection), bacterial infection, actinomycete infection (mycobacterial infection), fungal infection, decreased immunity (such as NK cell reduction) and anemia. In the United States, those medicines are even Black box marked due to some serious side effects, which include, for example, acute tuberculosis, invasive fungal infections, bacterial infections, and some lymphomas or other tumors. Research shows that currently available JAK inhibitors tend to have inhibitory activity on both JAK1 and JAK3, and most of these side effects are associated with inhibition of the activity of JAK3.

However, studies have shown that JAK family kinases are responsible for regulating numerous signaling pathways. Because of the fact that JAK1 and JAK3 are part of the common γ-chain cytokine receptor complex, development of JAK1 inhibitors with high selectivity is of great difficulty.

In summary, there is an urgent need in the art to develop inhibitors of Janus kinases or related kinases, especially high selectivity inhibitors for JAK1.

SUMMARY OF THE INVENTION

The object of the present invention is to provide a novel JAK enzyme inhibitor and the preparation and use thereof.

In the first aspect of the invention, a compound of the formula I, or a stereoisomer thereof, a tautomer thereof, or a pharmaceutically acceptable salt, hydrate or solvent thereof is provided:

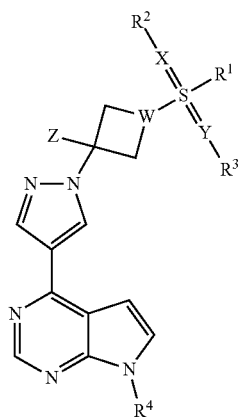

I

Wherein,

X is N or O;

Y is N or O;

Z is selected from the group consisting of substituted or unsubstituted $C_1$-$C_8$ alkyl;

W is N or C;

$R^1$, $R^2$ and $R^3$ are each independently selected from the group consisting of hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_6$-$C_{10}$ aryl (preferably phenyl), substituted or unsubstituted 5-10 membered (preferably 5- or 6-membered) heteroaryl having 1-3 heteroatoms selected from N, O, and S, and substituted or unsubstituted benzo 5-10 membered heteroaryl (preferably indolyl);

$R^4$ is selected from the following group: substituted or unsubstituted $C_1$-$C_6$ alkyl, substituted or unsubstituted $C_3$-$C_8$ cycloalkyl, substituted or unsubstituted 3-10 membered heterocycloalkyl with 1-3 heteroatoms selected from N, S and O, and $CH_2OR^5$, wherein $R^5$ is selected from the group consisting of: $C_1$-$C_6$ alkylcarbonyl and trialkylsilicyl;

in $R^1$, $R^2$, $R^3$, $R^4$ and Z, the substitution means substitution with one or more (such as 2, 3, 4, etc.) groups selected from the group consisting of halogen (preferably F), CN, $C_1$-$C_6$ alkyl, halogenated $C_1$-$C_6$ alkyl, and $C_1$-$C_6$ alkoxy.

In another preferred embodiment, the $XR^2$ and $YR^3$ are the same or different.

In another preferred embodiment, X is nitrogen, $YR^3$ is oxygen.

In another preferred embodiment, one or more of the $R^1$, $R^2$ and $R^3$ are independently selected from the group consisting of substituted or unsubstituted C1-C5 alkyl, substituted or unsubstituted C3-C5 cycloalkyl, and substituted or unsubstituted 3-5 membered heterocyclic group.

In another preferred embodiment, the 3-5 membered heterocyclic group has 1-2 heteroatoms selected from the group consisting of N, O and S.

In another preferred embodiment, the 3-5 membered heterocyclic group is aromatic or non-aromatic, and saturated or unsaturated (such as 4-5 membered heteroaryl ring group).

In another preferred embodiment, one or more of the $R^1$, $R^2$ and $R^3$ are independently selected from the group consisting of:

(a1) substituted or unsubstituted group selected from methyl, ethyl, propyl (including n-propyl, isopropyl), butyl (including n-, i-, and t-butyl), and pentyl:

(a2) substituted or unsubstituted group selected from cyclopropyl, cyclobutyl, and cyclopentyl;

(a3) substituted or unsubstituted group selected from oxopropyl, oxetanyl, tetrahydrofuryl, azacyclopropyl, azacyclobutyl, and azacyclopentyl;

wherein the substitution refers to substitution by one or more (such as 2, 3, 4, etc.) groups selected from the group consisting of F, Cl, Br, —OH, —CN, $NH_2$, =O, $C_1$-$C_3$ alkyl or $C_1$-$C_3$ haloalkyl.

In another preferred embodiment, at least one (such as 1 or 2) of $R^1$, $R^2$ and $R^3$ is selected from the group (a1), (a2) and (a3).

In another preferred embodiment, at least one (such as 1 or 2) of $R^1$, $R^2$ and $R^3$ is selected from the group consisting of C1-C4 alkyl, C1-C4 haloalkyl, cyclopropyl, and cyclobutyl.

In another preferred embodiment, $R^1$ and $R^2$ are each independently selected from the group consisting of C1-C5 alkyl (especially methyl, ethyl and propyl), C1-C5 haloalkyl (such as partially halogenated or perhalogenated alkyl, including (but not limited to): —$CF_3$, —$C_2H_4F$, —$C_2H_2F_3$, and —$C_2F_5$), cyclopropyl, cyclobutyl, oxopropyl, and oxetanyl.

In another preferred embodiment, when the formula I compound contains one or more chiral carbon atoms, the chiral carbon atom may be R configuration, S configuration, or the combination thereof.

In another preferred embodiment, in the formula I compound, the S atom adjacent with $XR^2$ and $YR^3$ may be chiral or achiral, and when the S atom is chiral, it can be R configuration, S configuration, or the combination thereof.

In another preferred embodiment, when $XR^2$ and $YR^3$ are different, the formula I compound is formula II or formula III compound:

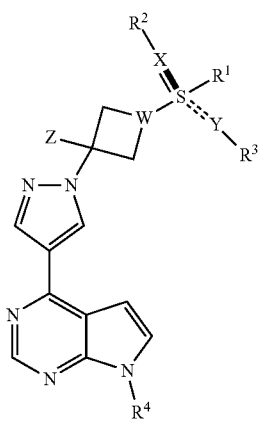

II

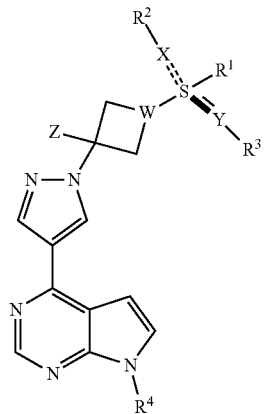

III in the formula II or formula III, $R^1$, $R^2$, $R^3$, $R^4$, W, X, Y and Z are as defined above.

In another preferred embodiment, W is N, X is nitrogen, $YR^3$ is oxygen, and the formula I compound is formula IV compound:

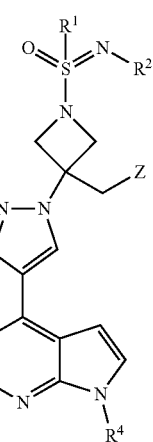

IV in the formula IV, $R^1$, $R^2$, $R^3$, $R^4$, W, X, Y and Z are as defined above.

In another preferred embodiment, the formula I compound is a racemate including an optically active compound formula V and formula VI compound:

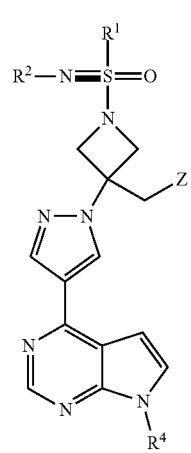

V

VI

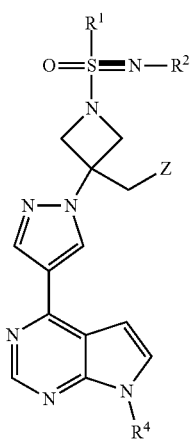

In the formula V or formula VI, R¹, R², R⁴ and Z are as defined above.

In another preferred embodiment, the formula I compound is formula VII compound:

VII

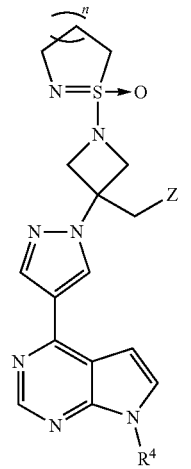

wherein n is a positive integer of 2-10; and R⁴ and Z are as defined above.

In another preferred embodiment, the compound of formula I is selected from the group consisting of:

| No. | Compound structure |
|---|---|
| LW104-A | |
| LW104-A-1 | R or S single isomer |
| LW104-A-2 | S or R single isomer |
| LW104-B | 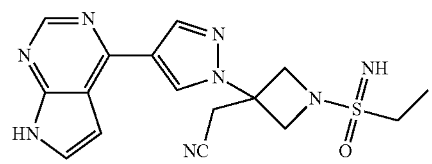 [SMILES: CCS(=N)(=O)N1CC(CC#N)(n2cc(-c3ncnc4[nH]ccc34)cn2)C1] |
| LW104-C | 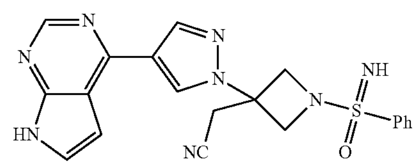 |
| LW104-C-1 | R or S single isomer |
| LW104-C-2 | S or R single isomer |
| LW104-D | 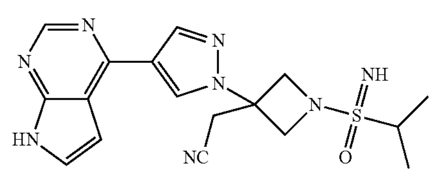 [SMILES: CC(C)S(=N)(=O)N1CC(CC#N)(n2cc(-c3ncnc4[nH]ccc34)cn2)C1] |
| LW104-D-1 | R or S single isomer |

| No. | Compound structure |
|---|---|
| LW104-D-2 | 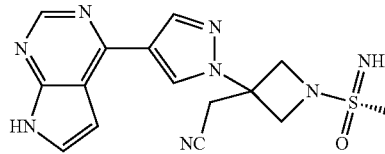 S or R single isomer |
| LW104-E | 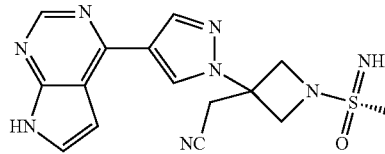 |
| LW104-E-1 | 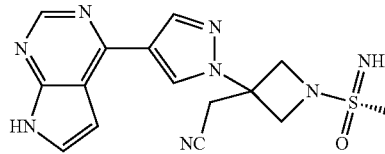 R or S single isomer |
| LW104-E-2 | 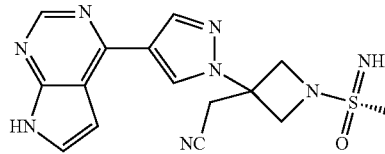 S or R single isomer |
| LW104-F | 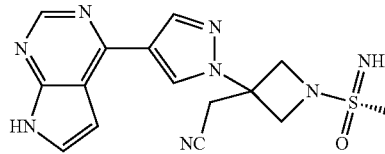 |
| LW104-F-1 | 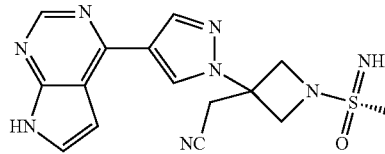 R or S single isomer |
| LW104-F-2 | 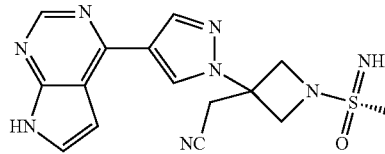 S or R single isomer |
| LW104-G | 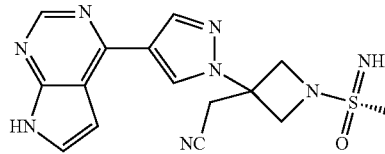 |
| No. | Compound structure |
|---|---|
| LW104-G-1 | 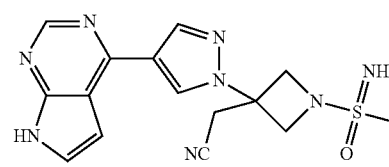 R or S single isomer |
| LW104-G-2 | 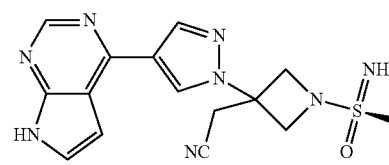 S or R single isomer |
| LW104-H | 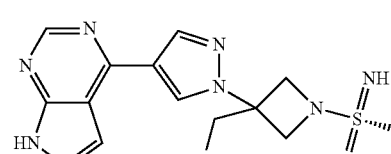 |
| LW104-H-1 | 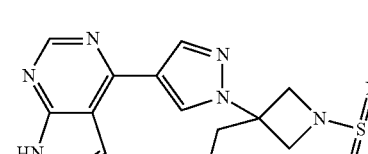 R or S single isomer |
| LW104-H-2 | 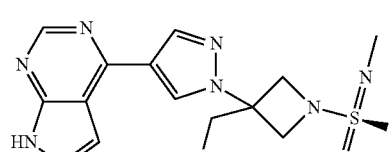 S or R single isomer |
| LW104-I | 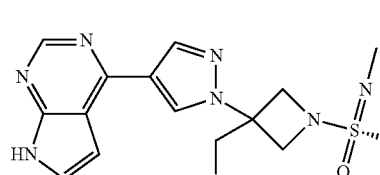 |
| LW104-I-1 | 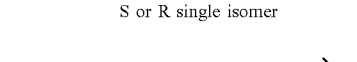 R or S single isomer |

| No. | Compound structure |
|---|---|
| LW104-I-2 | 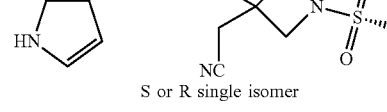 S or R single isomer |
| LW104-J | |
| LW104-K | |
| LW104-L | |
| LW104-L-1 | R or S single isomer |
| LW104-L-2 | S or R single isomer |
| LW104-M | |
| LW104-M-1 | R or S single isomer |
| No. | Compound structure |
|---|---|
| LW104-M-2 | 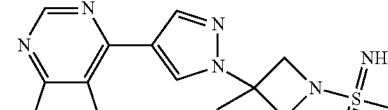 S or R single isomer |
| LW104-N | |
| LW104-N-1 | R or S single isomer |
| LW104-N-2 | S or R single isomer |
| LW104-O | |
| LW104-O-1 | R or S single isomer |
| LW104-O-2 | S or R single isomer |

| No. | Compound structure |
|---|---|
| LW104-P | 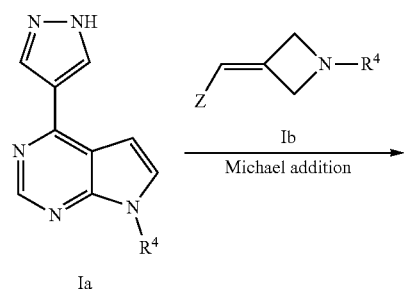 |
| LW104-P-1 | R or S single isomer |
| LW104-P-2 | S or R single isomer |
| LW104-Q | 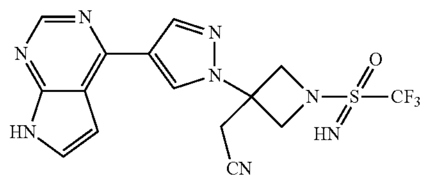 [SMILES: N#CCC1(n2cc(-c3ncnc4[nH]ccc34)cn2)CN(S(=N)(=O)C(F)(F)F)C1] |
| LW104-R | and |
| LW104-S | 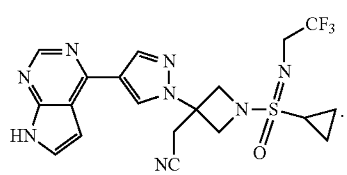 [SMILES: N#CCC1(n2cc(-c3ncnc4[nH]ccc34)cn2)CN(S(=O)(=NCC(F)(F)F)C2CC2)C1] |

In the second aspect of the invention, a method for preparing the compound of the formula I, or a stereoisomer thereof, a tautomer thereof, or a pharmaceutically acceptable salt, hydrate or solvent thereof of the first aspect of the present invention is provided, which comprising steps:

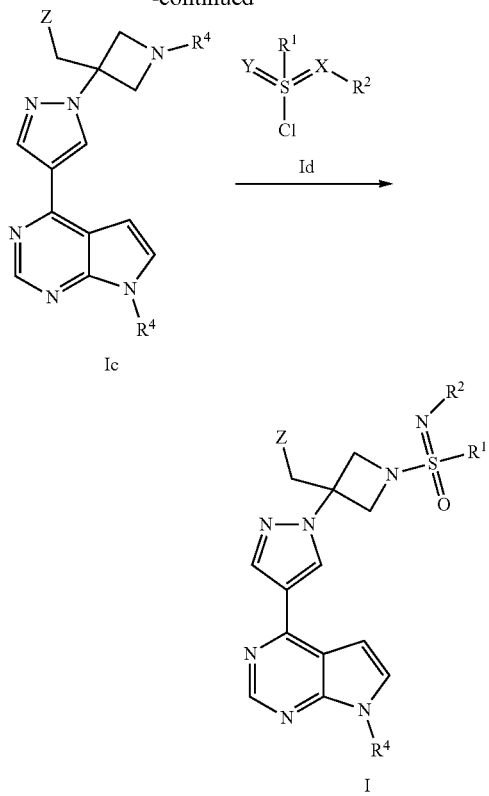

(i) in the presence of catalyst, reacting compound Ia with the formula Ib to produce compound Ic;

(ii) reacting compound Ic with Id to produce compound I, wherein the $R^1$, $R^2$, $R^4$, X, Y and Z are as defined in the first aspect of the present invention.

In another preferred embodiment, in the step (i), the catalyst is alkali.

In another preferred embodiment, in the step (i), the catalyst is selected from the group consisting of ammonium tetraalkylfluoride, ammonium tetraalkylhydroxide, guanidine, amidine, hydroxide, alkoxide, silicate, alkali metal phosphate, oxide, tertiary amine, alkali carbonate, alkali metal hydrogencarbonate, alkali metal hydrogenphosphate, phosphine or carboxylic acid alkali metal salt, and the combinations thereof.

In another preferred embodiment, the reaction is carried out in an organic solvent.

In another preferred embodiment, the organic solvent is selected from the group consisting of acetonitrile, dimethylacetamide, and a combination thereof.

In another preferred embodiment, the method is carried out at room temperature.

In another preferred embodiment, the reaction time of the method is 2-6 hour.

In another preferred embodiment, the formula Ic compound is of high yield and high purity.

In another preferred embodiment, the compound 1d is prepared from a compound selected from the group consisting of $PPh_3Cl_2$, phosphorus pentachloride, thionyl chloride, N-chlorosuccinimide, and the combinations thereof.

In another preferred embodiment, the step (ii) is carried out in the presence of base.

In another preferred embodiment, when $R^2$ and $R^4$ are hydrogen, the formula I compound is formula VIII compound, and the method comprises the step:

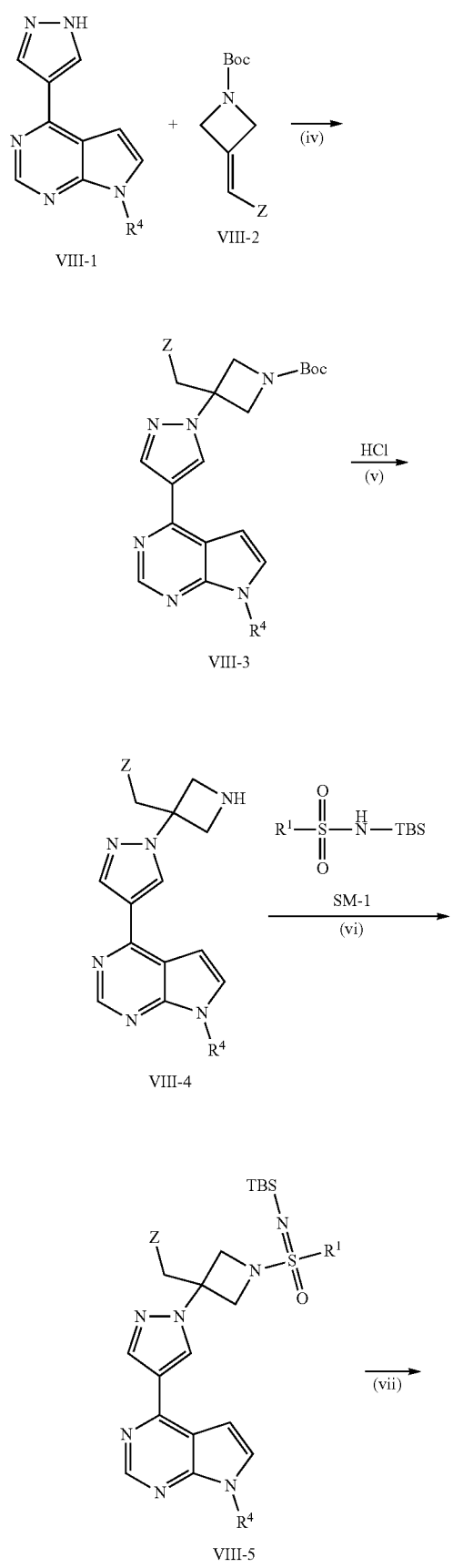

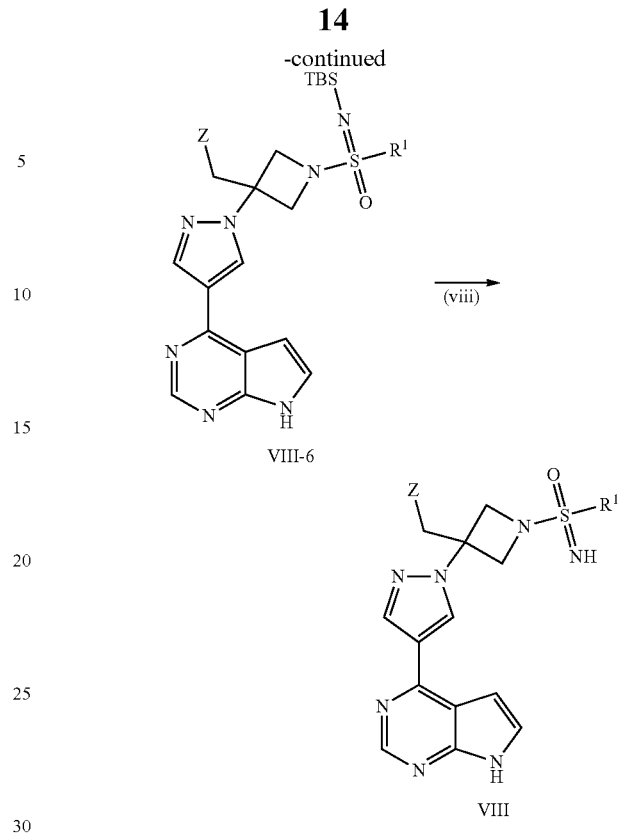

wherein the Z and $R^1$ are defined as in the first aspect of the invention.

In another preferred embodiment, in the step (iv), the compound VIII-1 is reacted with VIII-2 in the presence of base, wherein the base is an organic base or inorganic base.

In another preferred embodiment, the step (iv) is carried out in an organic solvent selected from acetonitrile and N,N-dimethylacetamide.

In another preferred embodiment, the step (v) is carried out under an acidic condition which is selected from the group consisting of aqueous hydrochloric acid solution, isopropanol hydrochloride solution, and dioxane hydrochloride solution.

In another preferred embodiment, the step (vi) is carried out in a chlorinating reagent selected from the group consisting of: $PPh_3Cl_2$, phosphorus pentachloride, thionyl chloride, N-chlorosuccinimide, and the combinations thereof.

In another preferred embodiment, the step (vii) is carried out in the presence of a base selected from the group consisting of ammonium tetraalkylfluoride, ammonium tetraalkylhydroxide, guanidine, amidine, hydroxide, alkoxide, silicate, alkali metal phosphate, oxide, tertiary amine, alkali carbonate, alkali metal hydrogencarbonate, alkali metal hydrogenphosphate, phosphine or carboxylic acid alkali metal salt, and the combinations thereof.

In another preferred embodiment, the step (vii) is carried out in the presence of an acid selected from the group consisting of hydrochloric acid, sulfuric acid, p-toluenesulfonic acid, tetraalkylammonium fluoride, and combinations thereof.

In another preferred embodiment, when $R^2$ is $C_1$-$C_6$ alkyl or $C_6$-$C_{10}$ aryl, the formula I compound is formula IX compound, and the method comprises the steps:

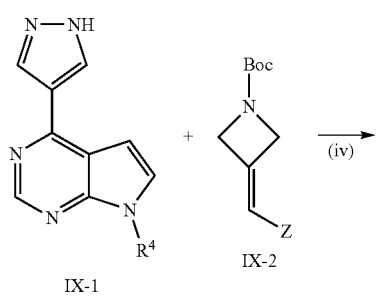

IX-1

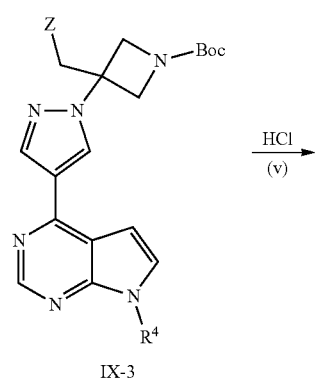

IX-3

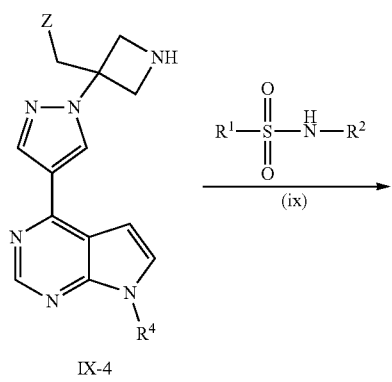

IX-4

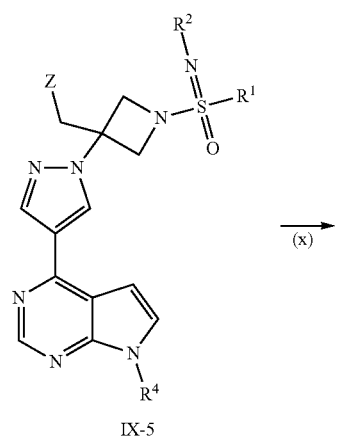

IX-5

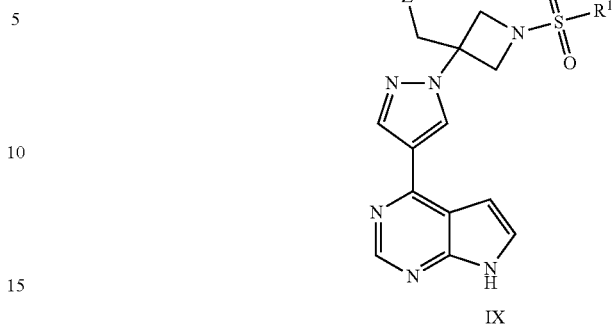

IX wherein the Z, $R^1$ and $R^4$ are defined as in the first aspect of the invention.

In another preferred embodiment, the step (ix) is carried out in a chlorinating reagent selected from the group consisting of: $PPh_3Cl_2$, phosphorus pentachloride, thionyl chloride, N-chlorosuccinimide, and the combinations thereof.

In another preferred embodiment, the step (x) is carried out in the presence of a base selected from the group consisting of ammonium tetraalkylfluoride, ammonium tetraalkylhydroxide, guanidine, amidine, hydroxide, alkoxide, silicate, alkali metal phosphate, oxide, tertiary amine, alkali carbonate, alkali metal hydrogencarbonate, alkali metal hydrogenphosphate, phosphine or carboxylic acid alkali metal salt, and the combinations thereof.

In the third aspect of the invention, compounds of the following structures are provided:

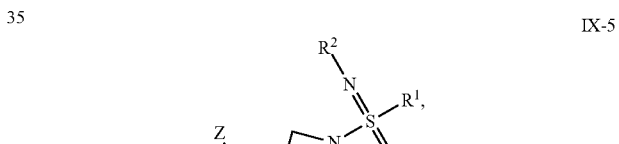

IX-5

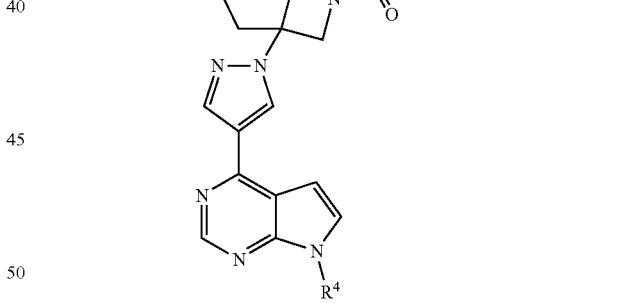

IX

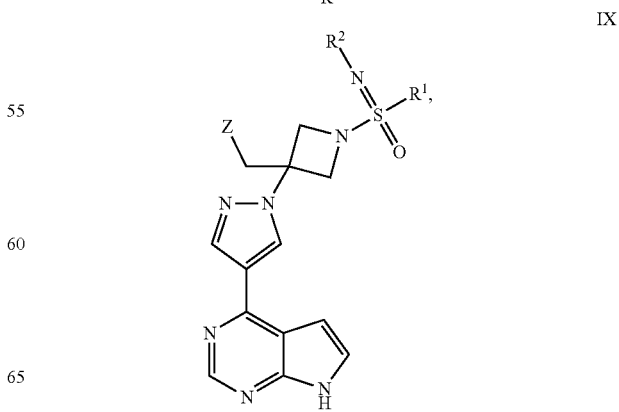

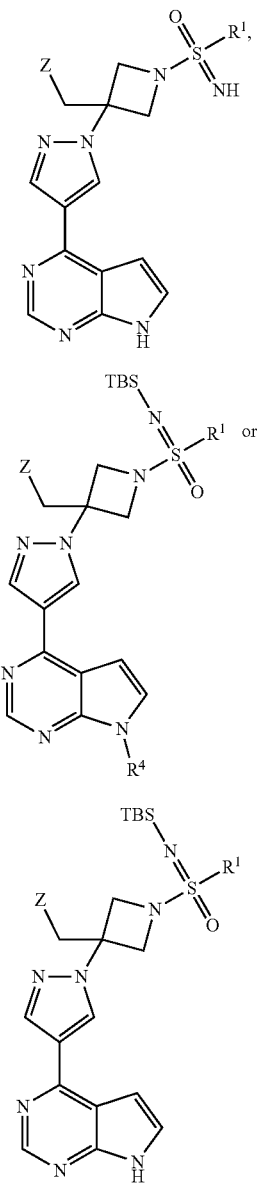

where the $R^1$, $R^2$, $R^4$, and Z are as defined in the first aspect of the present invention.

In the fourth aspect of the invention, a pharmaceutical composition is provided, which comprises (1) a compound according to the first aspect of the invention, or a stereoisomer or tautomer thereof, or a pharmaceutically acceptable salt, hydrate or solvate thereof; and (2) pharmaceutically acceptable carriers.

In another preferred embodiment, the pharmaceutical composition further comprises other JAK kinase inhibitors.

In another preferred embodiment, the other JAK kinase inhibitor may be selected from the group consisting of: tofartinib, ruxolitinib, and a combination thereof.

In the fifth aspect of the invention, a use of compound according to the first aspect of the invention, or a stereoisomer or tautomer thereof, or a pharmaceutically acceptable salt, hydrate or solvate thereof, or a use of the pharmaceutical composition according to the fourth aspect of the invention is provided, which is for the preparation of JAK kinase inhibitors.

It should be understood that, in the present invention, each of the technical features specifically described above and below (such as those in the Examples) can be combined with each other, thereby constituting new or preferred technical solutions which need not be specified again herein due to space limitations.

EMBODIMENTS FOR CARRYING OUT THE INVENTION

Through extensive and intensive research, the inventors have for the first time unexpectedly discovered a new JAK inhibitor with a novel structure and excellent bioactivity as well as excellent selectivity. Specifically, the selectivity of the compound of the present invention represented by the ratio of JAK3/JAK1 or the selectivity represented by the ratio of JAK3/JAK2 has been improved by about 100 folds. Therefore, the side effects of the compounds of the present invention associated with the inhibition of JAK3 are extremely significantly reduced, and the safety has been significantly improved. The present invention is completed on this basis.

Terms

Unless otherwise defined, all technical and scientific terms used herein have the same meaning as commonly understood by one of ordinary skill in the art to which this invention belongs.

As used herein, when used in reference to a particular recited value, the term "about" means that the value can vary by no more than 1% from the recited value. For example, as used herein, the expression "about 100" includes any value between 99 and 101 (for example, 99.1, 99.2, 99.3, 99.4, etc).

As used herein, the term "comprise" or "consist (consisting)" may be open, semi-closed and closed. In other words, the term also includes "consisting essentially of . . . ", or "constructed of . . . ."

Definitions

As used herein, the term "alkyl" includes straight or branched alkyl groups. For example, $C_1$-$C_8$ alkyl refers to straight or branched alkyls having from 1 to 8 carbon atoms, such as methyl, ethyl, propyl, isopropyl, butyl, isobutyl, tert-butyl, and the like.

As used herein, the term "alkenyl" includes a straight or branched alkenyl groups. For example, $C_2$-$C_6$ alkenyl refers to straight or branched alkenyl groups having 2-6 carbon atoms, such as vinyl, allyl, 1-propenyl, isopropenyl, 1-butenyl, 2-butenyl, and the like.

As used herein, the term "alkynyl" includes straight or branched alkynyl groups. For example, "C2-C6 alkynyl" refers to straight or branched alkynyls having 2 to 6 carbon atoms, such as ethynyl, propynyl, butynyl, and the like.

As used herein, "C3-$C_8$ cycloalkyl" refers to cycloalkyl groups having 3 to 8 carbon atoms. It may be a monocyclic ring, such as cyclopropyl, cyclobutyl, cyclopentyl, cyclohexyl, and the like. It may also be of bicyclic form, such as bridged or spiro ring form.

As used herein, "$C_1$-$C_8$ alkoxy" refers to a straight or branched alkoxy group having 1-8 carbon atoms; for example, methoxy, ethoxy, propoxy, isopropoxy, butoxy, isobutoxy, tert-butoxy, and the like.

As used herein, the term "3-10 membered heterocycloalkyl having 1-3 heteroatoms selected from the group consisting of N, S and O" refers to a saturated or partially saturated cyclic group having 3-10 atoms, wherein 1-3 atoms are heteroatoms selected from the group consisting of N, S and O. It may be a monocyclic ring or bicyclic form, such as bridged or spiro ring form. Specific examples may be oxetane, azetidine, tetrahydro-2H-pyranyl, piperidinyl, tetrahydrofuranyl, morpholinyl and pyrrolidinyl, and the like.

As used herein, "$C_6$-$C_{10}$ aryl" refers to aryl groups having 6 to 10 carbon atoms, such as phenyl, naphthyl, and the like.

As used herein, the term "5-10 membered heteroaryl having 1-3 heteroatoms selected from the group consisting of N, S and O" refers to cyclic aromatic groups having 5-10 atoms, of which 1-3 is selected from the group consisting of N, S and O. It may be a monocyclic ring or fused ring form. Specific examples may be pyridyl, pyridazinyl, pyrimidinyl, pyrazinyl, triazinyl, pyrrolyl, pyrazolyl, imidazolyl, (1,2,3)-triazolyl and (1,2,4)-triazolyl, tetrazyl, furyl, thienyl, isoxazolyl, thiazolyl, oxazolyl, etc.

Unless otherwise specified as "substituted or unsubstituted", the groups described in the present invention may be substituted with substituents selected from the group consisting of halogen, nitrile, nitro, hydroxy, amino, $C_1$-$C_6$ alkyl-amine, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_2$-$C_6$ alkenyl, halogenated $C_2$-$C_6$ alkynyl, halogenated $C_1$-$C_6$ alkoxy, allyl, benzyl, $C_6$-$C_{12}$ aryl, $C_1$-$C_6$ alkoxy-$C_1$-$C_6$ alkyl, $C_1$-$C_6$ alkoxy-carbonyl, phenoxycarbonyl, $C_2$-$C_6$ alkynyl-carbonyl, $C_2$-$C_6$ alkenyl-carbonyl, $C_3$-$C_6$ cycloalkyl-carbonyl, $C_1$-$C_6$ alkyl-sulfonyl, etc.

As used herein, "halogen" or "halogen atom" refers to F, Cl, Br, and I. More preferably, the halogen or halogen atom is selected from F, Cl and Br. "Halogenated" means substituted by atoms selected from the group consisting of F, Cl, Br, and I.

Unless otherwise stated, the structural formula described herein are intended to include all isomeric forms (such as enantiomeric, diastereomeric, and geometric isomers (or conformational isomers)): for example, R, S configuration of asymmetrical centers, (Z), (E) isomers of double bonds, etc.

Therefore, the single stereochemical isomers or enantiomers, diastereomers or geometric isomers (or conformers) of the compounds of the invention, or mixtures thereof all fall within the scope of the invention.

As used herein, the term "tautomer" means that structural isomers having different energies can exceed the low energy barrier and thereby transform between each other. For example, proton tautomers (proton shift) includes interconversion by proton transfer, such as 1H-carbazole and 2H-carbazole. Valence tautomers include interconversion through some bonding electron recombination.

As used herein, the term "solvate" refers to a complex of specific ratio formed by a compound of the invention coordinating to a solvent molecule.

As used herein, the term "hydrate" refers to a complex formed by the coordination of a compound of the invention with water.

Active Ingredients

As used herein, "compound of the invention" refers to the compound of the formula (I), as well as various crystal forms of the compound of the formula (I), the pharmaceutically acceptable salts, hydrate or solvates thereof.

As used herein, "pharmaceutically acceptable salts" refers to salts suitable for use in pharmaceutical which is formed by compound of the present invention with an acid or base.

The pharmaceutically acceptable salts include inorganic and organic salts. Preferred type of salts are salts formed by the compounds of the present invention and acid. Suitable salt-forming acids include, but are not limited to: inorganic acids such as hydrochloric acid, hydrobromic acid, hydrofluoric acid, sulfuric acid, nitric acid, phosphoric acid; organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid and the like: and acidic amino acids such as aspartic acid, glutamic acid and the like.

Compound of Formula I

The novel JAK inhibitors prepared by the present invention, i.e., the formula I compounds are as shown in the following table A:

TABLE A list of the Compound I of the present invention

| No. | Compound structure | Remarks |
| --- | --- | --- |
| LW104-A | (structure) | $^1$HNMR (400 MHz, d6-DMSO): δ 3.03 (q, J = 6.4 Hz, 1H), 3.63 (s, 3H), 4.06 (dd, J = 8.0, 4.8 Hz, 2H), 4.16 (s, 1H), 4.43 (d, J = 9.2 Hz, 2H), 7.07 (d, J = 2.8 Hz. 1H), 7.61 (s, 1H), 8.45 (s, 1H) 8.70 (s, 1H), 8.91 (s, 1H), 12.13 (br, 1H). |
| LW104-A-1 | (structure)<br>R or S single isomer | $^1$HNMR (400 MHz, d6-DMSO): δ 3.03 (q, J = 6.4 Hz. 1H), 3.63 (s, 3H), 4.06 (dd, J = 8.0, 4.8 Hz, 2H), 4.16 (s, 1H), 4.43 (d, J = 9.2 Hz, 2H), 7.07 (d, J = 2.8 Hz, 1H), 7.61 (s, 1H), 8.45 (s, 1H), 8.70 (s, 1H), 8.91 (s, 1H), 12.13 (br, 1H). |

TABLE A-continued list of the Compound I of the present invention

| No. | Compound structure | Remarks |
|---|---|---|
| LW104-A-2 | S or R single isomer | $^1$HNMR (400 MHz, d6-DMSO): δ 3.03 (q, J = 6.4 Hz, 1H), 3.63 (s, 3H), 4.06 (dd, J = 8.0, 4.8 Hz, 2H), 4.16 (s, 1H), 4.43 (d, J = 9.2 Hz, 2H), 7.07 (d, J = 2.8 Hz, 1H), 7.61 (s, 1H), 8.45 (s, 1H), 8.70 (s, 1H), 8.91 (s, 1H), 12.13 (br, 1H). |
| LW104-B | 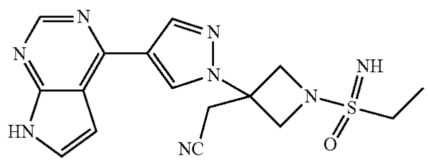 [SMILES: CCS(=N)(=O)N1CC(CC#N)(n2cc(-c3ncnc4[nH]ccc34)cn2)C1] | $^1$HNMR (400 MHz, d6-DMSO): δ 1.23 (t, J = 6.4 Hz, 3H), 3.03 (q, J = 6.4 Hz, 1H), 3.63 (s, 2H), 4.06 (dd, J = 8.0, 4.8 Hz, 2H), 4.16 (s, 1H), 4.43 (d, J = 9.2 Hz, 2H), 7.07 (d, J = 2.8 Hz, 1H), 7.61 (s, 1H), 8.45 (s, 1H), 8.70 (s, 1H), 8.91 (s, 1H), 12.13 (br 1H) MS-ESI: [M + Na]$^+$ = 393 |
| LW104-C | 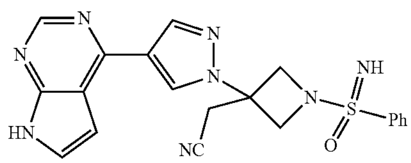 [SMILES: N#CCC1(n2cc(-c3ncnc4[nH]ccc34)cn2)CN(S(=N)(=O)c2ccccc2)C1] | $^1$HNMR (400 MHz, d6-DMSO): δ 3.97 (dd, J = 9.6, 4.8Hz, 2H), 4.21 (t, J = 9.6 Hz, 2H), 4.74 (s, 1H), 5.28 (t, J = 4.8 Hz, 2H), 6.96 (d, J = 1.6 Hz, 1H), 7.20-7.23 (m, 1H), 7.36 (d, J = 8.8 Hz, 1H), 7.52-7.53 (m, 3H), 7.57 (t, J = 7.2 Hz, 1H), 7.85-7.88 (m, 2H), 8.25 (s, 1H), 8.62 (d, J = 8.0 Hz, 1H), 12.09 (br, 1H). MS-ESI: [M − H]$^+$ = 417. |
| LW104-C-1 | R or S single isomer | $^1$HNMR (400 MHz, d6-DMSO): δ 3.97 (dd, J = 9.6, 4.8 Hz, 2H), 4.21 (t, J = 9.6 Hz, 2H), 4.74 (s, 1H), 5.28 (t, J = 4.8 Hz, 2H), 6.96 (d, J = 1.6 Hz, 1H). 7.20-7.23 (m, 1H), 7.36 (d, J = 8.8 Hz, 1H), 7.52-7.53 (m, 3H), 7.57 (t, J = 7.2 Hz, 1H), 7.85-7.88 (m, 2H), 8.25 (s, 1H), 8.62 (d, J = 8.0 Hz, 1H), 12.09 (br, 1H). MS-ESI: [M − H]$^+$ = 417 |
| LW104-C-2 | S or R single isomer | $^1$HNMR (400MHz, d6-DMSO): δ 3.97 (dd, J = 9.6, 4.8 Hz, 2H), 4.21 (t, J = 9.6 Hz, 2H), 4.74 (s, 1H), 5.28 (t, J = 4.8 Hz, 2H), 6.96 (d, J = 1.6 Hz, 1H), 7.20-7.23 (m, 1H), 7.36 (d, J = 8.8 Hz, 1H), 7.52-7.53 (m, 3H), 7.57 (t, J = 7.2 Hz, 1H), 7.85-7.88 (m, 2H), 8.25 (s, 1H), 8.62 (d, J = 8.0 Hz. 1H), 12.09 (br, 1H). MS-ESI: [M − H]$^+$ = 417 |
| LW104-D | 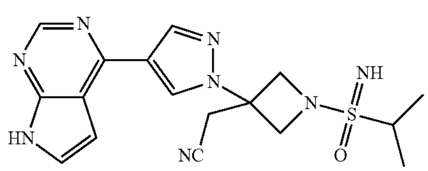 [SMILES: CC(C)S(=N)(=O)N1CC(CC#N)(n2cc(-c3ncnc4[nH]ccc34)cn2)C1] | $^1$HNMR(400 MHz, d6-DMSO): δ 1.23-1.25 (m, 6H), 3.10-3.20 (m, 1H), 3.64 (s, 2H), 4.02 (dd, J = 15.6, 8.4 Hz, 2H), 4.45 (dd, J = 15.6, 8.4 Hz, 2H), 7.07 (d, J = 2.0 Hz, 1H), 7.60-7.62 (m, 1H), 8.44 (s, 1H). 8.70 (s. 1H), 8.90 (s, 1H), 12.16 (br. 1H) MS-ESI: [M + Na]$^+$ = 407. |
| LW104-D-1 | R or S single isomer | $^1$HNMR (400MHz, d6-DMSO): δ 1.23-1.25 (m, 6H), 3.10-3.20 (m, 1H), 3.64 (s, 2H), 4.02 (dd, J = 15.6, 8.4 Hz, 2H), 4.45 (dd, J = 15.6, 8.4 Hz, 2H), 7.07 (d, J = 2.0 Hz, 1H), 7.60-7.62 (m, 1H), 8.44 (s, 1H), 8.70 (s, 1H). 8.90 (s, 1H), 12.16 (br, 1H). MS-ESI: [M + Na]$^+$ = 407. |
| LW104-D-2 | S or R single isomer | $^1$HNMR (400 MHz, d6-DMSO): δ 1:23-1.25 (m, 6H), 3.10-3.20 (m, 1H), 3.64 (s, 2H), 4.02 (dd, J = 15.6, 8.4 Hz, 2H), 4.45 (dd, J = 15.6, 8.4 Hz, 2H), 7.07 (d, J = 2.0 Hz, 1H), 7.60-7.62 (m, 1H), 8.44 (s, 1H). 8.70 (s, 1H), 8.90 (s, 1H), 12.16 (br, 1H). MS-ESI: [M + Na]$^+$ = 407. |

TABLE A-continued list of the Compound I of the present invention

| No. | Compound structure | Remarks |
|---|---|---|
| LW104-E | 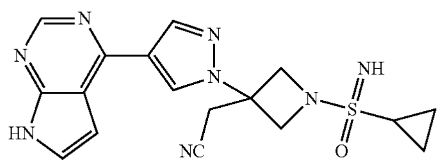 | ¹HNMR (400 MHz, d6-DMSO): δ 0.86-0.91 (m, 2H), 1.10-1.15 (m, 2H), 2.58-2.61 (m, 1H), 3.59 (s, 2H), 4.02 (s, 2H), 4.09 (s, J = 9.6 Hz, 2H), 4.46 (dd, J = 9.2. 1.6 Hz, 2H), 7.04 (d, J = 2.0 Hz, 1H), 7.58 (d, J = 3.2 Hz, 1H), 8.42 (s, 1H), 8.67 (s, 1H), 8.89 (s, 1H), 12.10 (br, 1H). MS-ESI: [M + H]⁺ = 383. |
| LW104-E-1 | R or S single isomer | ¹HNMR (400 MHz, d6-DMSO): δ 0.86-0.91 (m, 2H), 1.10-1.15 (m, 2H), 2.58-2.61 (m, 1H), 3.59 (s, 2H), 4.02 (s, 2H). 4.09 (s, J = 9.6 Hz, 2H), 4.46 (dd, J = 9.2, 1.6 Hz, 2H), 7.04 (d, J = 2.0 Hz, 1H), 7.58 (d, J = 3.2 Hz, 1H), 8.42 (s, 1H). 8.67 (s, 1H), 8.89 (s, 1H), 12.10 (br, 1H). MS-ESI: [M + H]⁺ = 383. |
| LW104-E-2 | S or R single isomer | ¹HNMR (400 MHz, d6-DMSO): δ 0.86-0.91 (m, 2H), 1.10-1.15 (m, 2H), 2.58-2.61 (m, 1H), 3.59 (s, 2H). 4.02 (s, 2H), 4.09 (s, J = 9.6 Hz, 2H), 4.46 (dd, J = 9.2, 1.6 Hz, 2H), 7.04 (d, J = 2.0 Hz, 1H), 7.58 (d, J = 3.2 Hz, 1H), 8.42 (s, 1H), 8.67 (s, 1H), 8.89 (s, 1H), 12.10 (br, 1H). MS-ESI: [M+H]⁺ = 383. |
| LW104-F | 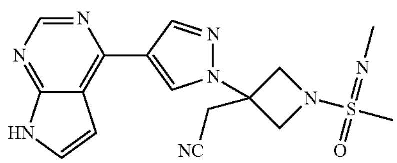 [SMILES: CN=S(C)(=O)N1CC(CC#N)(n2cc(-c3ncnc4[nH]ccc34)cn2)C1] | ¹HNMR (400 MHz, d6-DMSO): δ 2.56 (s, 3H), 3.00 (s, 3H), 3.67 (s, 2H), 4.16 (d, J = 9.2 Hz, 2H), 4.53 (dd, J = 14.8, 9.2 Hz, 2H), 7.08 (d, J = 2.8 Hz, 1H), 7.61-7.62 (m, 1H), 8.47 (s, 1H), 8.71 (s, 1H), 8.92 (s, 1H), 12.03 (br, 1H). MS-ESI: [M + Na]⁺ = 393. |
| LW104-F-1 | R or S single isomer | ¹HNMR (400 MHz, d6-DMSO): δ 2.56 (s, 3H), 3 00 (s, 3H), 3.67 (s, 2H), 4.16 (d, J = 9.2 Hz, 2H), 4.53 (dd, J = 14.8. 9.2 Hz, 2H), 7.08 (d, J = 2.8 Hz, 1H), 7.61-7.62 (m, 1H), 8.47 (s, 1H), 8.71 (s, 1H), 8.92 (s, 1H), 12.03 (br, 1H). MS-ESI: [M + Na]⁺ = 393. |
| LW104-F-2 | S or R single isomer | ¹HNMR (400 MHz, d6-DMSO): δ 2.56 (s, 3H), 3.00 (s, 3H), 3.67 (s, 2H), 4.16 (d, J = 9.2 Hz, 2H). 4.53 (dd, J = 14.8. 9.2 Hz, 2H), 7.08 (d, J = 2.8 Hz, 1H), 7.61-7.62 (m, 1H), 8.47 (s, 1H), 8.71 (s, 1H), 8.92 (s, 1H), 12.03 (br, 1H). MS-ESI: |[M + H]⁺ = 393. |
| LW104-G | 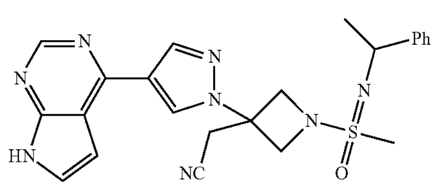 [SMILES: CC(N=S(C)(=O)N1CC(CC#N)(n2cc(-c3ncnc4[nH]ccc34)cn2)C1)c1ccccc1] | ¹HNMR (400 MHz, d6-DMSO): δ 1.29-1.33 (m, 3H), 3.04 (s, 3H), 3.49 (d, J = 12.8 Hz, 2H), 3.58 (d, J = 9.2 Hz, 1H), 4.00 (d, J = 8.8 Hz, 1H). 4.14 (d, J = 8.8 Hz, 1H), 4.38 (d, J = 9.2 Hz, 1H), 4.57 (q, J = 6.8 Hz, 1H). 7.05 (d, J = 2.4 Hz, 1H), 7.16-7.17 (m, 1H), 7.24-7.28 (m, 2H), 7.35-7.36 (m, 2H), 7.60-7.62 (m, 1H), 8.41 (s, 1H). 8.70 (s, 1H), 8.77 (s, 1H), 12.14 (br, 1H). MS-ESI: [M - H]⁺= 459. |
| LW104-G-1 | R or S single isomer | MS-ESI: |M - H]⁺ = 459. |

TABLE A-continued list of the Compound I of the present invention

| No. | Compound structure | Remarks |
| --- | --- | --- |
| LW104-G-2 | S or R single isomer | MS-ESI: [M − H]⁺ = 459. |
| LW104-H | 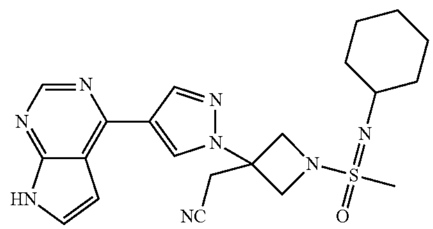 [SMILES: CS(=O)(=NC1CCCCC1)N1CC(CC#N)(n2cc(-c3ncnc4[nH]ccc34)cn2)C1] | ¹HNMR(400 MHz, d6-DMSO): δ 1.07-1.29 (m, 6H), 1.61-1.70 (m, 4H), 2.98 (s, 3H), 3.188-3.23 (m, 1H). 3.65 (s, 2H), 4.14 (t, J = 8.4 Hz, 2H), 4.51 (dd, J = 9.2, 6.0 Hz, 2H), 7.09 (dd, J = 3.2, 0.8 Hz, 1H), 7.61 (t, J = 2.8 Hz, 1H), 8.47 (s, 1H), 8.70 (s, 1H), 8.91 (s, 1H), 12.14 (br, 1H). MS-ESI: [M − H]⁺ = 437 |
| LW104-H-1 | 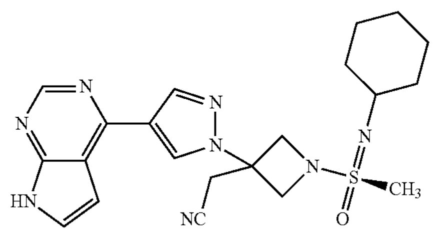 [SMILES: C[S@](=O)(=NC1CCCCC1)N1CC(CC#N)(n2cc(-c3ncnc4[nH]ccc34)cn2)C1] | ¹HNMR (400 MHz, d6-DMSO): δ 1.07-1.29 (m, 6H), 1.61-1.70 (m, 4H), 2.98 (s, 3H), 3.18-3.23 (m, 1H), 3.65 (s, 2H), 4.14 (t, J = 8.4 Hz, 2H), 4.51 (dd, J = 9.2, 6.0 Hz, 2H), 7.09 (dd, J = 3.2, 0.8 Hz, 1H). 7.61 (t, J = 2.8 Hz, 1H), 8.47 (s, 1H), 8.70 (s, 1H), 8.91 (s, 1H), 12.14 (br, 1H). MS-ESI: [M − H]⁺ = 437 |
| LW104-H-2 | S or R single isomer | ¹HNMR (400 MHz, d6-DMSO): δ 1.07-1.29 (m, 6H), 1.61-1.70 (m, 4H), 2.98 (s, 3H). 3.18-3.23 (m, 1H), 3.65 (s, 2H). 4.14 (t, J = 8.4 Hz, 2H), 4.51 (dd, J = 9.2, 6.0 Hz, 2H), 7.09 (dd, J = 3.2, 0.8 Hz, 1H), 7.61 (t, J = 2.8 Hz, 1H). 8.47 (s, 1H), 8.70 (s, 1H), 8.91 (s, 1H), 12.14 (br, 1H), MS-ESI: [M−H]⁺ = 437 |
| LW104-I | 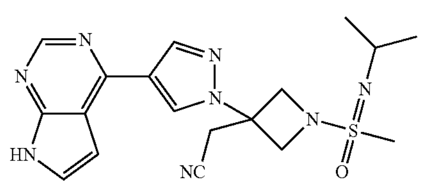 [SMILES: CC(C)N=S(C)(=O)N1CC(CC#N)(n2cc(-c3ncnc4[nH]ccc34)cn2)C1] | ¹HNMR (400 MHz, d6-DMSO): δ 1.03 (dd, J = 6.4, 2.0 Hz, 6H), 1.08 (s, 9H), 2.98 (s, 3H), 3.55-3.58 (m, 1H), 3.65 (s, 2H), 4.15 (dd, J = 9.2, 4.0 Hz, 2H). 4.51 (d, J = 8.8 Hz, 2H), 7.22 (d, J = 3.6 Hz, 1H), 7.76 (d, J = 3.6 Hz, 1H), 8 47 (s, 1H), 8.71 (s, 1H), 8.92 (s, 1H), 12.14 (br, 1H). MS-ESI: [M − H]⁺ = 397. |
| LW104-I-1 | R or S single isomer | ¹HNMR (400 MHz, d6-DMSO): δ 1.03 (dd, J = 6.4, 2.0 Hz, 6H), 1.08 (s, 9H), 2.98 (s, 3H), 3.55-3.58 (m, 1H), 3.65 (s, 2H), 4.15 (dd, J = 9.2, 4.0 Hz, 2H), 4.51 (d, J = 8.8 Hz, 2H), 7.22 (d, J = 3.6 Hz, 1H), 7.76 (d, J = 3.6 Hz, 1H), 8.47 (s, 1H), 8.71 (s, 1H), 8.92 (s, 1H), 12.14 (br, 1H). MS-ESI: [M − H]⁺ = 397. |
| LW104-I-2 | S or R single isomer | ¹HNMR(400 MHz, d6-DMSO): δ 1.03 (dd, J = 6.4, 2.0 Hz, 6H), 1.08 (s, 9H), 2.98 (s, 3H), 3.55-3.58 (m, 1H), 3.65 (s, 2H), 4.15 (dd, J = 9.2, 4.0 Hz, 2H), 4.51 (d, J = 8.8 Hz, 2H), 7.22 (d, J = 3.6 Hz, 1H), 7.76 (d, J = 3.6 Hz, 1H), 8.47 (s, 1H), 8.71 (s, 1H), 8.92 (s, 1H), 12.14 (br, 1H), MS-ESI: [M − H]⁺ = 397. |

TABLE A-continued list of the Compound I of the present invention

| No. | Compound structure | Remarks |
| --- | --- | --- |
| LW104-J | 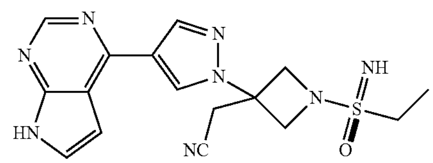 [SMILES: CCS(=N)(=O)N1CC(CC#N)(n2cc(-c3ncnc4[nH]ccc34)cn2)C1] | $^1$HNMR (400 MHz, d6-DMSO) δ 1.23 (t, J = 6.4 Hz, 3H), 3.03 (q, J = 6.4 Hz, 1H), 3.63 (s, 2H), 4.06 (dd, J = 8.0, 4.8 Hz, 2H), 4.16 (s, 1H), 4.44 (d, J = 9.2 Hz, 2H), 7.08 (d, J = 2.8 Hz, 1H), 7.62 (s, 1H), 8.46 (s, 1H), 8.71 (s, 1H), 8.92 (s, 1H), 12.14 (br, 1H) MS-ESI: [M + Na]$^+$ = 393 |
| LW104-K | 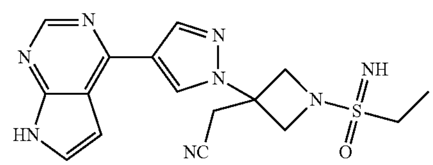 [SMILES: CCS(=N)(=O)N1CC(CC#N)(n2cc(-c3ncnc4[nH]ccc34)cn2)C1] | $^1$HNMR (400 MHz, d6-DMSO): δ 1.23 (t, J = 6.4 Hz, 3H), 3.04 (q, J = 6.4 Hz, 1H), 3.63 (s, 2H), 4.06 (dd, J = 8.0. 4.8 Hz, 2H), 4.16 (s, 1H), 4.45 (d, J = 9.2 Hz, 2H), 7.08 (d, J = 2.8 Hz, 1H), 7.61 (s, 1H), 8.45 (s, 1H), 8.71 (s, 1H), 8.91 (s, 1H), 12.13 (br, 1H). MS-ESI [M + Na]$^+$ = 393 |
| LW104-L | 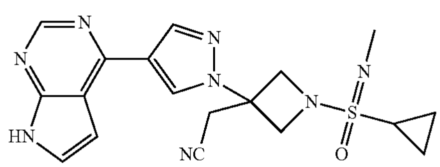 [SMILES: CN=S(=O)(C1CC1)N1CC(CC#N)(n2cc(-c3ncnc4[nH]ccc34)cn2)C1] | $^1$H NMR (400 MHz, DMSO-d$_6$) δ 12.15 (s, 1H), 8.94 (s, 1H), 8.71 (s, 1H), 8.47 (s, 1H), 7.62 (dd, J = 3.5, 2.3 Hz, 1H), 7.09 (dd, J = 3.6, 1.7 Hz, 1H), 4.60 (dd, J = 9.2, 4.5 Hz. 2H), 4.19 (dd, J = 9.1, 2.3 Hz, 2H), 3.67 (s, 2H), 2.77 (m, J = 12.7, 6.3, 5.8 Hz, IH), 2.59 (s, 3H), 1.06-0.99 (m, 1H), 0.96-0.87 (m, 3H). MS-ESI [M + H]$^+$ = 397 |
| LW104-L-1 | R or S single isomer | $^1$H NMR (400 MHz, DMSO-d$_6$) δ 12.15 (s, 1H), 8.94 (s, 1H), 8.71 (s, 1H), 8 47 (s, 1H), 7.62 (dd, J = 3.5, 2.3 Hz, 1H), 7.09 (dd, J = 3.6, 1.7 Hz, IH), 4.60 (dd, J = 9.2, 4.5 Hz, 2H). 4.19 (dd, J = 9.1, 2.3 Hz, 2H), 3.67 (s, 2H), 2.77 (m, J = 12.7, 6.3, 5.8 Hz, 1H), 2.59 (s, 3H), 1.06-0.99 (m, 1H), 0.96-0.87 (m, 3H). MS-ESI: [M + H]$^+$ = 397 |
| LW104-L-2 | S or R single isomer | $^1$H NMR (400 MHz, DMSO-d$_6$) δ 12.15 (s, 1H), 8.94 (s, 1H), 8.71 (s, 1H). 8.47 (s, 1H), 7.62 (dd, J = 3.5, 2.3 Hz, 1H), 7.09 (dd, J = 3.6, 1.7 Hz. 1H). 4.60 (dd, J = 9.2, 4.5 Hz, 2H), 4.19 (dd, J = 9.1, 2.3 Hz, 2H), 3.67 (s, 2H), 2.77 (m, J = 12.7, 6.3, 5.8 Hz. 1H), 2.59 (s, 3H), 1.06-0.99 (m, 1H), 0.96-0.87 (m, 3H). MS-ESI: [M + H]$^+$ = 397 |
| LW104-M | 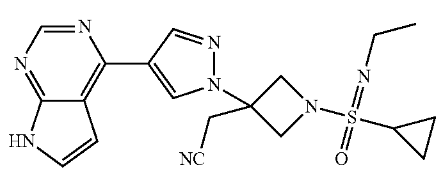 [SMILES: CCN=[S@](=O)(C1CC1)N1CC(CC#N)(n2cc(-c3ncnc4[nH]ccc34)cn2)C1] | $^1$H NMR (400 MHz, DMSO-d$_6$) δ 12.14 (s, 1H), 8.93 (s, 1H), 8.71 (s, 1H), 8.47 (s, 1H),7.62 (dd. J = 3.6, 2.4 Hz, 1H). 7.09 (dd, J = 3.6, 1.7 Hz, 1H), 4.59 (dd, J = 9.2, 3.7 Hz, 2H), 4.18 (dd, J = 9.1, 4.6 Hz, 2H), 3.66 (s, 2H), 2.99 (q, J = 7.1 Hz, 2H), 2.81-2.71 (m. 1H), 1.04 (t, J = 7.2 Hz, 3H), 0.92 (m, 4H). MS-ESI: [M + H]$^+$ = 411 |
| LW104-M-1 | R or S single isomer | $^1$H NMR (400 MHz, DMSO-d$_6$) δ 12.14 (s, 1H), 8.93 (s, 1H), 8.71 (s, 1H), 8.47 (s, 1H), 7.62 (dd, J = 3.6, 2.4 Hz. 1H), 7.09 (dd, J = 3.6, 1.7 Hz, 1H), 4.59 (dd, J = 9.2, 3.7 Hz. 2H). 4.18 (dd, J = 9.1, 4.6 Hz, 2H), 3.66 (s, 2H), 2.99 (q, J = 7.1 Hz, 2H), 2.81-2.71 (m, 1H), 1.04 (t, J = 7.2 Hz, 3H). 0.92 (m, 4H). MS-ESI: [M + H]$^+$ = 411 |

TABLE A-continued list of the Compound I of the present invention

| No. | Compound structure | Remarks |
|---|---|---|
| LW104-M-2 | S or R single isomer | ¹H NMR (400 MHz, DMSO-d₆) δ 12.14 (s, 1H), 8.93 (s, 1H). 8.71 (s. 1H), 8.47 (s, 1H), 7.62 (dd, J = 3.6, 2.4 Hz, 1H), 7.09 (dd, J = 3.6, 1.7 Hz. 1H), 4.59 (dd, J = 9.2, 3.7 Hz, 2H), 4.18 (dd, J = 9.1, 4.6 Hz, 2H), 3.66 (s, 2H). 2.99 (q, J = 7.1 Hz, 2H), 2.81-2.71 (m, 1H), 1.04 (t, J = 7.2 Hz, 3H), 0.92 (m, 4H).<br>MS-ESI: [M + H]⁺ = 411 |
| LW104-N | 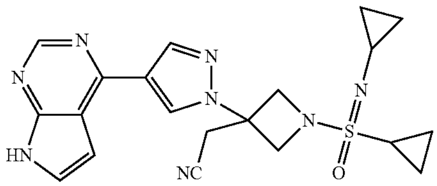 [SMILES: N#CCC1(n2cc(-c3ncnc4[nH]ccc34)cn2)CN([S@](=O)(=NC2CC2)C2CC2)C1] | ¹H NMR (400 MHz, DMSO-d₆) δ 12.14 (s, 1H), 8.95 (s, 1H), 8.71 (s, 1H), 8.47 (s. 1H), 7.62 (dd, J = 3.6, 1.7 Hz, 1H), 7.09 (dd, J = 3.4, 1.5 Hz, 1H), 4.62 (d, J = 8.8 Hz, 2H), 4.23 (dd, J = 9.2, 4.9 Hz, 2H), 3.66 (s, 2H), 2.74 (m, 1H), 2.53 (d, J = 4.3 Hz, 1H), 1.07-0.97 (m, 1H), 0.96-0.84 (m, 3H), 0.48-0.37 (m, 2H), 0.35-0.22 (m, 2H).<br>MS-ESI: [M + H]⁺ = 423 |
| LW104-N-1 | R or S single isomer | ¹H NMR (400 MHz, DMSO-d₆) δ 12.14 (s, 1H), 8.95 (s, 1H), 8.71 (s, 1H). 8.47 (s, 1H), 7.62 (dd, J = 3.6, 1.7 Hz, 1H), 7.09 (dd, J = 3.4, 1.5 Hz, 1H), 4.62 (d, J = 8.8 Hz, 2H), 4.23 (dd, J = 9.2, 4.9 Hz, 2H), 3.66 (s, 2H), 2.74 (m, 1H). 2.53 (d, J = 4.3 Hz, 1H), 1.07-0.97 (m, 1H), 0.96-0.84 (m, 3H), 0.48-0.37 (m, 2H), 0.35-0.22 (m, 2H).<br>MS-ESI: [M + H]⁺ = 423 |
| LW104-N-2 | S or R single isomer | ¹H NMR (400 MHz, DMSO-d₆) δ 12.14 (s, 1H), 8.95 (s, 1H), 8.71 (s, 1H), 8.47 (s, 1H), 7.62 (dd, J = 3.6, 1.7 Hz, 1H), 7.09 (dd, J = 3.4, 1.5 Hz, 1H), 4.62 (d, J = 8.8 Hz, 2H), 4.23 (dd, J = 9.2, 4.9 Hz, 2H), 3.66 (s, 2H), 2.74 (m, 1H). 2.53 (d, J = 4.3 Hz, 1H), 1.07-0.97 (m, 1H), 0.96-0.84 (m, 3H), 0.48-0.37 (m, 2H), 0.35-0.22 (m, 2H).<br>MS-ESI: [M + H]⁺ = 423 |
| LW104-O | 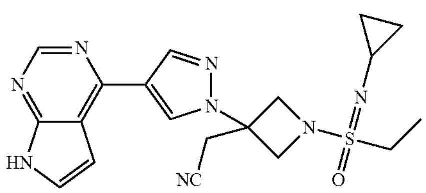 [SMILES: CC[S@@](=O)(=NC1CC1)N1CC(CC#N)(n2cc(-c3ncnc4[nH]ccc34)cn2)C1] | ¹H NMR (400 MHz, DMSO-d₆) δ 12.16 (s, 1H), 8.94 (s, 1H), 8.71 (s, 1H). 8.48 (s, 1H), 7.83-7.44 (m, 1H), 7.10 (dd, J = 3.4, 1.5 Hz, 1H), 4.59 (dd, J = 9.1, 2.7 Hz, 2H), 4.19 (dd, J = 9.1, 3.1 Hz, 2H), 3.68 (s, 2H), 3.15 (q, J = 7.2 Hz, 2H), 2.55 (dd, J = 7.1, 3.7 Hz, 1H). 1.21 (t, J = 73 Hz, 3H), 0.57-0.13 (m, 4H).<br>MS-ESI: [M + H]⁺ = 411 |
| LW104-O-1 | R or S single isomer, or | ¹H NMR (400 MHz, DMSO-d₆) δ 12.16 (s, 1H), 8.94 (s, 1H), 8.71 (s, 1H), 8.48 (s, 1H), 7.83-7.44 (m, 1H), 7.10 (dd, J = 3.4, 1.5 Hz, 1H), 4.59 (dd, J = 9.1, 2.7 Hz, 2H), 4.19 (dd, J = 9.1, 3.1 Hz, 2H), 3.68 (s, 2H), 3.15 (q, J = 7.2 Hz, 2H), 2.55 (dd, J = 7.1, 3.7 Hz, 1H), 1.21 (t, J = 7.3 Hz, 3H), 0.57-0.13 (m. 4H).<br>MS-ESI: [M + H]⁺ = 411 |
| LW104-O-2 | S or R single isomer | ¹H NMR (400 MHz, DMSO-d₆) δ 12.16 (s, 1H), 8.94 (s, 1H), 8.71 (s, 1H), 8.48 (s, 1H), 7.83-7.44 (m, 1H), 7.10 (dd, J = 3.4, 1.5 Hz, 1H), 4.59 (dd, J = 9.1, 2.7 Hz, 2H), 4.19 (dd, J = 9.1, 3.1 Hz, 2H), 3.68 (s, 2H), 3.15 (q, J = 7.2 Hz, 2H), 2.55 (dd, J = 7.1, 3.7 Hz, 1H), 1.21 (t, J = 7.3 Hz, 3H), 0.57-0.13 (m, 4H).<br>MS-ESI: [M-H]⁺ = 411 |

TABLE A-continued list of the Compound I of the present invention

| No. | Compound structure | Remarks |
|---|---|---|
| LW104-P | 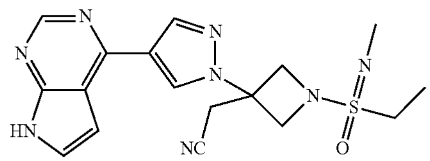 [SMILES: CCS(=O)(=NC)N1CC(CC#N)(n2cc(-c3ncnc4[nH]ccc34)cn2)C1] | ¹HNMR (400 MHz, d6-DMSO): δ 1.23 (t, J = 6.4 Hz, 3H), 2.56 (s, 3H), 3.02 (q, J = 6.4 Hz, 2H), 3.63 (s, 2H), 4.16 (d, J = 9.2 Hz, 2H), 4.53 (dd, J = 14.8, 9.2 Hz, 2H), 7.08 (d, J = 2.8 Hz, 1H), 7.61 (s, 1H), 8.45 (s, 1H), 8.71 (s, 1H), 8.91 (s, 1H), 12.1 (br, 1H). MS-ESI: [M + H]⁺ = 385 |
| LW104-P-1 | R or S single isomer | ¹HNMR(400 MHz, d6-DMSO): δ 1.23 (t, J = 6.4 Hz, 3H), 2.56 (s, 3H), 3.02 (q, J = 6.4 Hz, 2H), 3.63 (s, 2H), 4.16 (d, J = 9.2 Hz, 2H), 4.53 (dd, J = 14.8, 9.2 Hz, 2H), 7.08 (d, J = 2.8 Hz, 1H), 7.61 (s, 1H), 8.45 (s, 1H), 8.71 (s, 1H), 8.91 (s, 1H), 12.1 (br, 1H). MS-ESI: [M + H]⁺ = 385 |
| LW104-P-2 | S or R single isomer | ¹HNMR (400 MHz, d6-DMSO): δ 1.23 (t, J = 6.4 Hz, 3H), 2.56 (s, 3H), 3.02 (q, J = 6.4 Hz, 2H), 3.63 (s, 2H), 4.16 (d, J = 9.2 Hz, 2H), 4.53 (dd, J = 14.8, 9.2 Hz, 2H). 7.08 (d, J = 2.8 Hz, 1H), 7.61 (s, 1H), 8.45 (s, 1H), 8.71 (s, 1H), 8.91 (s, 1H), 12.1 (br, 1H). MS-ESI: [M + H]⁺ = 385 |
| LW104-Q | 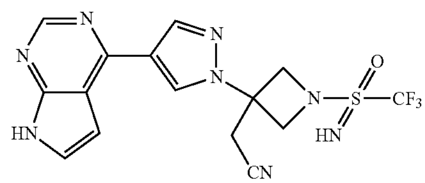 [SMILES: N#CCC1(n2cc(-c3ncnc4[nH]ccc34)cn2)CN(S(=N)(=O)C(F)(F)F)C1] | MS-ESI: [M + H]⁺ = 411 |
| LW104-R | 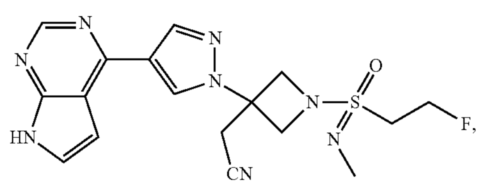 | MS-ESI: [M + H]⁺ = 403 |
| LW104-S | 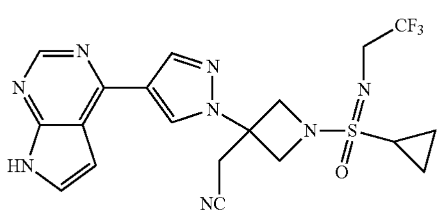 | MS-ESI: [M + H]⁺ = 465 |

Pharmaceutical Composition and the Administration Thereof

Since the compound of the present invention has excellent inhibitory activity against JAK kinase, the compound of the present invention and various crystal forms thereof, pharmaceutically acceptable inorganic or organic salts, hydrates or solvates, and pharmaceutical compositions containing the compounds of the present invention as main active ingredients can be used for preventing and/or treating (stabilizing, alleviating or curing) JAK kinase-related diseases (for example, skin diseases, rheumatoid arthritis, multiple sclerosis, type I diabetes, psoriatic arthritis, juvenile arthritis, Crohn's disease, myasthenia gravis, cancers including prostate cancer, kidney cancer, liver cancer, breast cancer, lung cancer, thyroid cancer, Kaposi's sarcoma, giant lymphoproliferative, pancreatic cancer, leukemia, lymphoma or multiple myeloma, etc.).

The pharmaceutical composition of the invention comprises the compound of the present invention in a safe and effective dosage range and pharmaceutically acceptable excipients or carriers. Wherein the "safe and effective dosage" means that the amount of compound is sufficient to significantly improve the condition without causing serious side effects. Generally, the pharmaceutical composition contains 1-2000 mg compound of the invention per dose, preferably, 10-200 mg compound of the invention per dose. Preferably, the "dose" is a capsule or a tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes (but is not limited to): oral administration and parenteral (intravenous, intramuscular or subcutaneous) administration.

Solid dosage forms for oral administration include capsules, tablets, pills, powders and granules. In these solid dosage forms, the active compounds are mixed with at least one conventional inert excipient (or carrier), such as sodium citrate or $Ca_2HPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum: (c) humectant, such as, glycerol: (d) disintegrating agents such as agar, calcium carbonate, potato starch or tapioca starch, alginic acid, certain composite silicates, and sodium carbonate; (e) dissolution-retarding agents, such as paraffin: (f) absorption accelerators, for example, quaternary ammonium compounds: (g) wetting agents, such as cetyl alcohol and glyceryl monostearate: (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

Compounds of the present invention can be administrated alone, or in combination with any other pharmaceutically acceptable compounds (such as anti-HBV agents).

In the case of co-administration, the pharmaceutical composition can also include one or more (2, 3, 4, or more) other pharmaceutically acceptable compounds (such as anti-HBV agents). The one or more (2, 3, 4, or more) other pharmaceutically acceptable compounds (e.g., anti-HBV agents) may be used simultaneously, separately or sequentially with the compound of the present invention so as to prevent and/or treat HBV infection or HBV related diseases.

When the pharmaceutical compositions are used, a safe and effective amount of compound of the present invention is applied to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

The Main Advantages of the Present Invention are:

1. The compounds of the invention are novel in structure, and have excellent JAK kinase inhibitor activity;

2. The compounds of the invention are more specific for the inhibition of JAK1.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are weight parts and weight percentage.

The experimental materials and reagents used in the following examples are available from commercially available sources unless otherwise specified.

General Materials and Test Methods:

The instruments and materials involved in the examples are as follows:

The NMR hydrogen spectrum was obtained by Bruker AV-400 (400 MHz) nuclear magnetic analyzer.

Chemical shifts were recorded with tetramethylsilane as an internal standard and showed by ppm as unit ($CDCl_3$: δ 7.26 ppm). The recorded data information were as follows: chemical shifts and the splitting and coupling constants thereof (s: single peak; d: double peak; t: triplet; q: quadruple peak; br: wide peak; m: multiple peak).

Unless otherwise needed, mass spectrometry data was analyzed by liquid-mass spectrometer from Finigan Advanced LCQ (Finnigan LCQ Advantage), wherein all the reactions were operated under dry argon-protected anhydrous anaerobic conditions. The solid metal organic compound was stored in an argon-protected dry box.

Tetrahydrofuran and diethyl ether were obtained by distillation, and sodium metal and benzophenone were added thereto during distillation. Dichloromethane, pentane and hexane were treated with calcium hydride.

The special raw materials and intermediates involved in the present invention were provided by Tianjin Changsen Pharmaceutical Co., Ltd., and other chemical reagents were purchased from reagent suppliers such as Shanghai Chemical Reagent Company, Aldrich Company, Acros Company, etc. If the intermediate or product required for the reaction in the synthesis was insufficient for the next step, the synthesis was repeated for a plurality of times until sufficient amount is prepared.

The raw materials and reagents according to the present invention can be purchased commercially or custom-made, unless otherwise specified.

The compounds of the invention may contain one or more asymmetric centers, so the series of compounds may be in racemic or single enantiomeric form. The compounds prepared by the present invention (formula IV) was heterocyclic compounds with a purity higher than 95%, and the structural characterization of each final product was determined by MS or/and hydrogen spectrum nuclear magnetic resonance (1H NMR) analysis, respectively. The synthesis of various compounds and intermediates of the present invention is illustrated by the following examples.

Example 1: Synthesis of Compound 1a

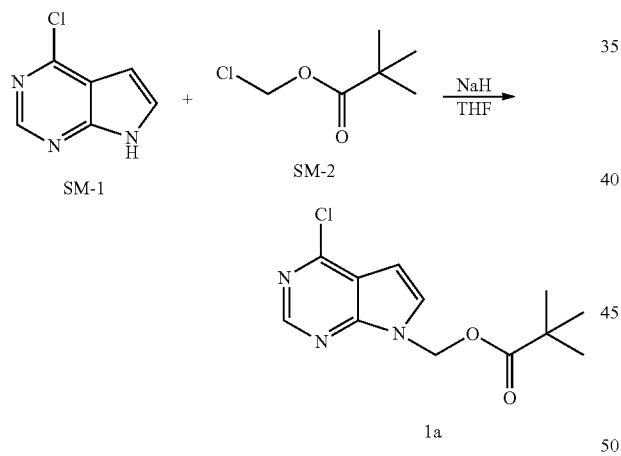

Under argon protection, 4-chloropyrrolopyridine (308 g, 2.0 mol, SM-1) was dissolved in 1.5 L anhydrous DMAc, cooled to 10° C. in ice water bath, and added to NaH (104 g, 2.6 mol, 60%) in batches. The temperature was kept at 10-15° C., and the mixture was stirred for 1 h under the temperature after the dropwise addition was completed. A solution of methyl pivalate in tetrahydrofuran (390 g, 2.6 mol dissolved in 1.5 L anhydrous tetrahydrofuran, SM-2) was slowly added dropwise, and the temperature was maintained below 20° C., and the addition was ended after 1 h. The reaction solution was warmed to room temperature and reacted for 2 h, and the TLC showed the reaction was completed. The reaction was quenched by being added with water drop wise in ice-water bath, and extracted with methyl t-butyl ether. The organic phase was concentrated to obtain white solid 1a (530 g).

Example 2: Synthesis of Compound 2a

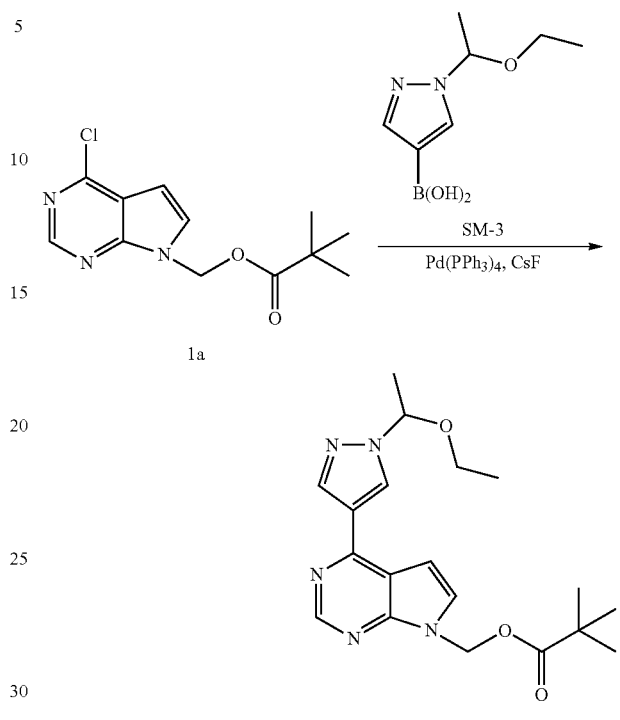

Compound 1a (309 g, 1.16 mol), 1-(1-ethoxyethyl)-4-pyrazole boronic acid pinacol ester (339 g, 1.28 mol, SM-3), cesium fluoride (352 g, 2.32 mol), n-butanol (1.5 L), water (1.5 L) were added into a three-necked flask. After the system was replaced with argon for three times, tetrakis (triphenylphosphine) palladium was added (10 g, 12 mmol). After replaced with argon once more, the mixture was warmed to reflux and reacted for 16 h, and HPLC showed the reaction is complete. The layers were separated after cooling, extracted with ethyl acetate, concentrated and directly supplied to the next step (with n-butanol).

Example 3: Synthesis of Compound 3a

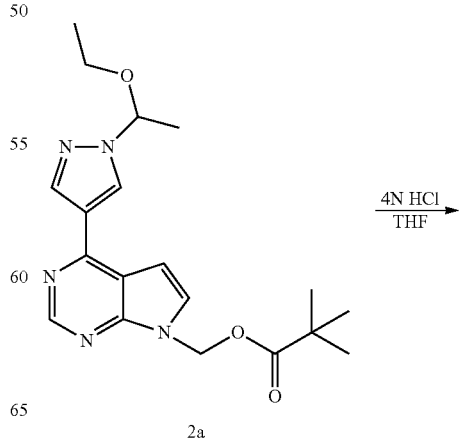

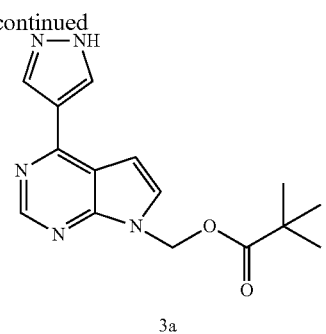

3a

Compound 2a was dissolved in 500 mL tetrahydrofuran, and 4N hydrochloric acid solution (800 mL) was added dropwise, reacted at room temperature overnight, and HPLC showed that the starting material was consumed, and purity of target compound was 73.1%. 10% sodium hydroxide solution was slowly added drop wise in ice-water bath until pH=7-8, and a large amount of solid was generated. After filtration, the filter cake was rinsed with water, oven dried to obtain solid 3a (193 g), purity 92%, and the yield of the two-steps was 56%.

Example 4: Synthesis of Compound 4a

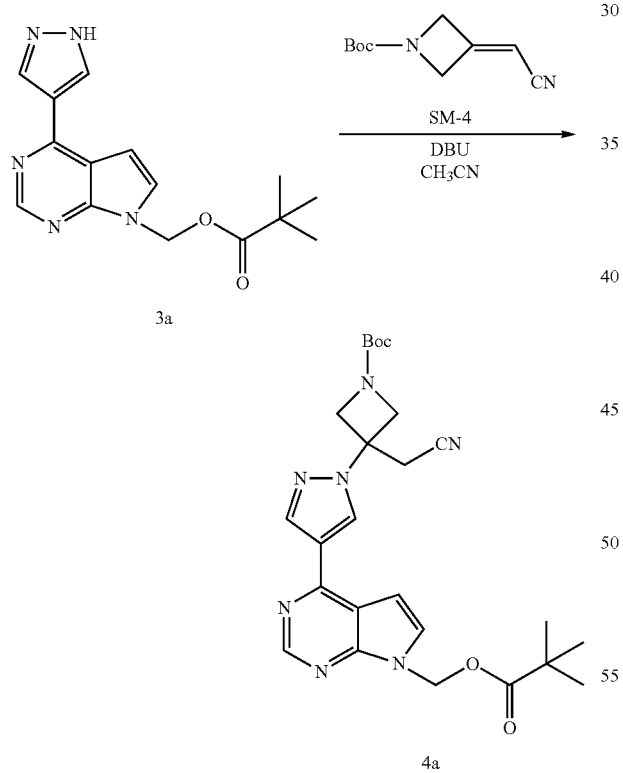

Compound 3a (189 g) and tert-butyl 3-(cyanomethylene) azetidin-1-carboxylic acid (184 g, SM-4) were added to acetonitrile (1 L), cooled in ice water bath, and added to DBU. The mixture was maintained under the temperature to react for 0.5 h, and then reacted under room temperature for 4 h. A large amount of solid was precipitated. MTBE 500 mL was added, stirred for 10 min after filtration, and the filter cake was washed with MTBE. Dried in oven at 45° C. overnight, and solid 4a (254 g) was produced; yield 81%, purity 95%.

Example 5: Synthesis of Compound 5a

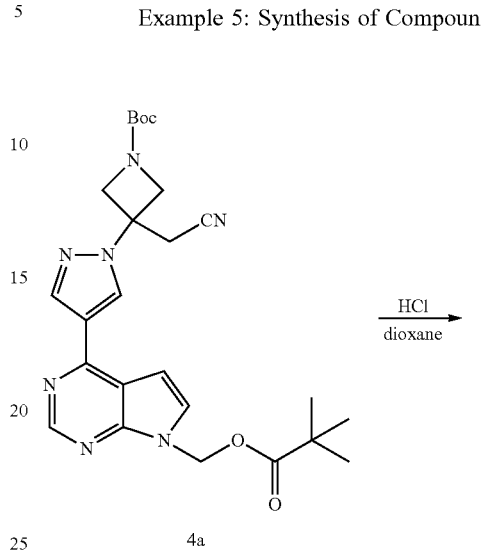

4a

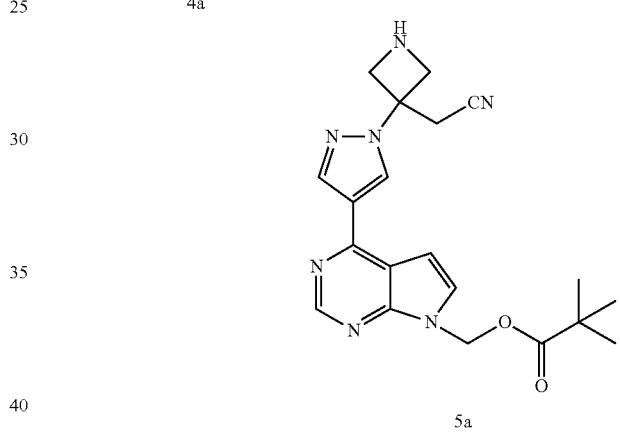

5a

Compound 4a (240 g) was dissolved in dichloromethane (1 L), and 4M HCl/dioxane solution (500 ml) was added drop wise in ice water bath and reacted overnight. Under 0° C., 5% ammonia solution was added to adjust pH to 8-10, extracted with dichloromethane, dried and concentrated. Pulped with acetone for 2 h, filtered (slowly), and the filter cake was washed with MTBE, dried to obtain white solid 114 g, purity 97%. The filtrate was concentrated and pulped with acetonitrile. A white solid was obtained (56.6 g) after filtration and drying, purity 95%. Two-part yield was 88.9%.

Example 6: Synthesis of Ph$_3$PCl$_2$ Chloroform Suspension

Under nitrogen protection, triphenylphosphine (2.89 g, 11 mmol) and hexachloroethane (2.60 g, 11 mmol) were added to chloroform (30 ml) and heated to 70° C. to react for 18 hours. Solid was precipitated and 0.36M Ph$_3$PCl$_2$ chloroform suspension was obtained after cooling.

Example 7: Synthesis of Compound 1b

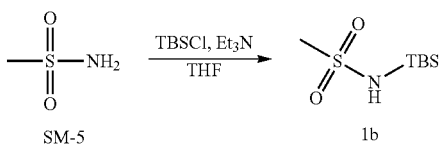

Under nitrogen, the SM-5 (0.939 g, 9.9 mmol) was dissolved in anhydrous THF (15 ml), and Et₃N (2.75 ml, 19.8 mmol) was added at room temperature. After stirred for 5 min, TBSCl (1.73 g, 11.5 mmol) in toluene (5 ml) solution was added dropwise, and solid was precipitated. The mixture was stirred at room temperature overnight, filtrated, concentrated and column chromatography purified to obtain white solid 800 mg.

Example 8: Synthesis of Compound 2b

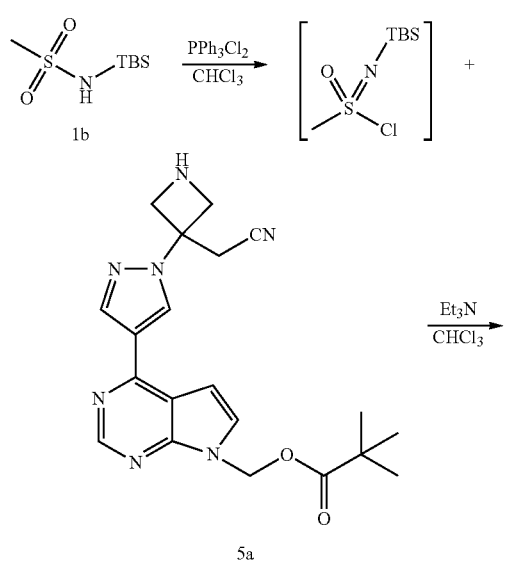

Under the protection of nitrogen, 0.36M Ph₃PCl₂/chloroform suspension (8.8 ml, 3.18 mmol) was cooled to 0° C., and triethylamine (482 mg, 4.77 mmol) was added and stirred for 15 min. Compound 1b (709 mg, 3.0 mmol) was added at 0° C. After stirred for 20 min, the compound 5a (200 mg, 0.53 mmol) was added to the above reaction system, and the reaction was warmed to room temperature and stirred overnight. TLC showed that some of the starting material had not been consumed. The reaction was quenched by being added with water, and extracted with ethyl acetate. Organic phase was concentrated and column chromatography separated, eluent (n-heptane/ethyl acetate=1:1, and followed by CH₂Cl₂/MeOH=30/1), to provide white solid.

Example 9: Synthesis of Compound 3b

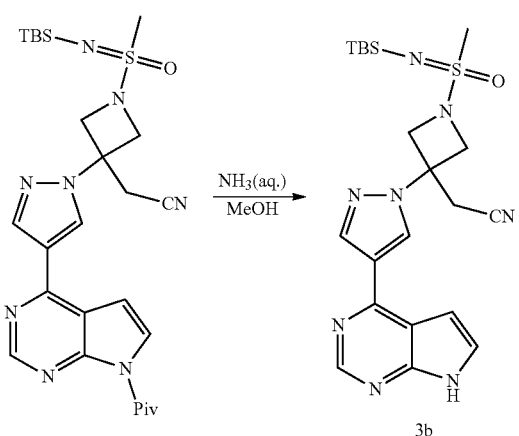

The compound 2b (3.9 g) was dissolved in methanol (50 ml), and ammonia water (25 ml) was added at room temperature. Some of the raw materials were precipitated, and the solid was gradually dissolved as the reaction progressed. After reacted for 18 h, TLC showed that the material was consumed. The reaction solution was extracted with EA, dried and concentrated, and separated by column chromatography (mobile phase: n-heptane/EA=1:1) to obtain white solid 3b (760 mg), yield 30%.

Example 10: Synthesis of Compound LW104-A

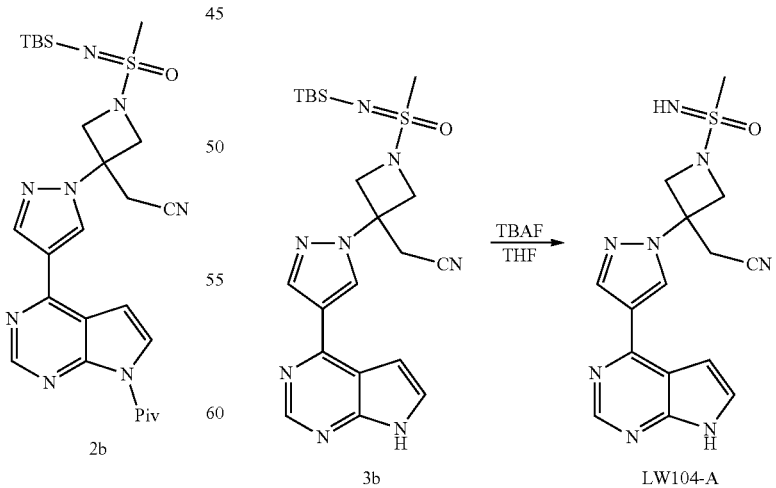

The compound (35 mg) was dissolved in 5 mL of tetrahydrofuran, and tetrabutylammonium fluoride (44 mg) was added thereto. After stirred at room temperature for 0.5 h, TLC showed that some of the material was not consumed. A portion of TBAF was added, and the reaction was continued for 0.5 h. After completion of the reaction, the reaction was quenched by being added with water, and extracted with ethyl acetate. The organic phase was washed with saturated brine and dried over anhydrous sodium sulfate, and concentrated and column chromatography purified (heptane/EA=20/1) to provide white solid 10 mg. $^1$HNMR (400 MHz, d6-DMSO): δ 3.03 (q, J=6.4 Hz, 1H), 3.63 (s, 3H), 4.06 (dd, J=8.0, 4.8 Hz, 2H), 4.16 (s, 1H), 4.43 (d, J=9.2 Hz, 2H), 7.07 (d, J=2.8 Hz, 1H), 7.61 (s, 1H), 8.45 (s, 1H), 8.70 (s, 1H), 8.91 (s, 1H), 12.13 (br, 1H).

Example 11: Synthesis of Compound 1c

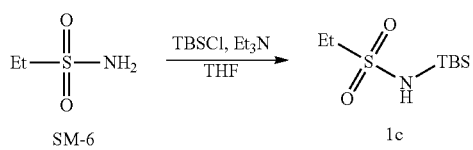

Preparation of the compound was as described in Example 7 for 1b. The material used in this example was SM-6, and compound 1c was obtained after purification.

Example 12: Synthesis of Compound 2c

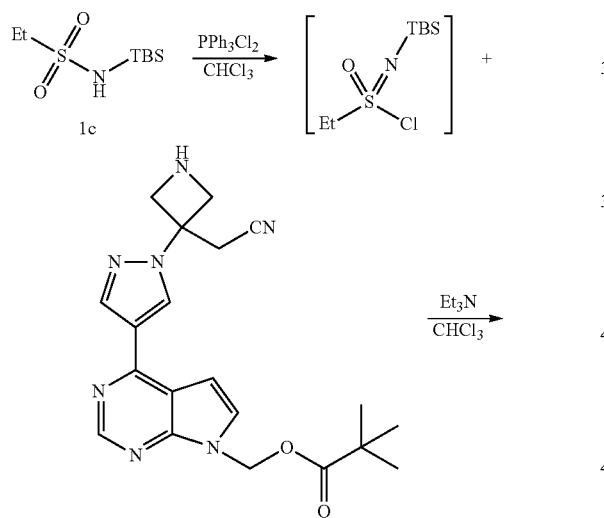

Preparation of the compound was as described in Example 8 for 2b, the material used in this example was 1c, and compound 2c was obtained after purification.

Example 13: Synthesis of Compound 3c

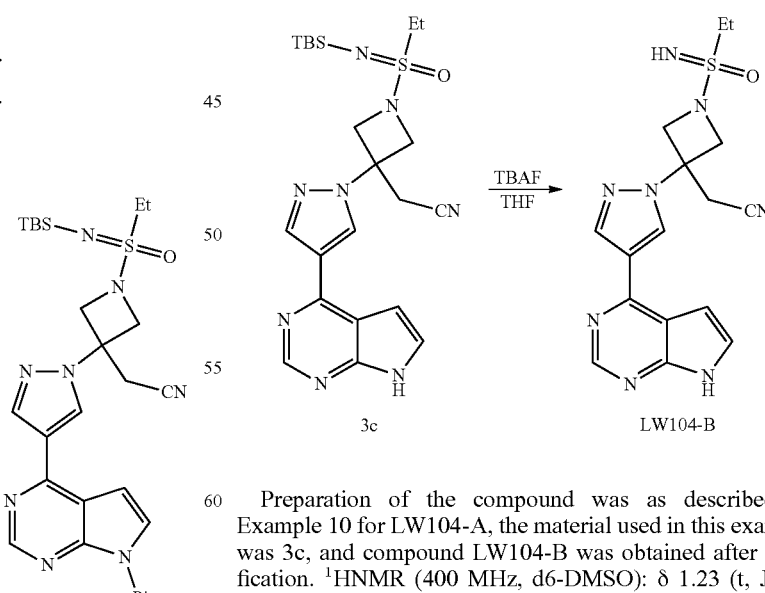

Preparation of the compound was as described in Example 9 for 3b, the material used in this example was 2c, and compound 3c was obtained after purification. $^1$HNMR (400 MHz, d6-DMSO): δ 0.01 (s, 3H), 0.03 (s, 3H), 0.83 (s, 9H), 1.23 (t, J=8.0 Hz, 3H), 3.00-3.07 (m, 1H), 3.63 (s, 2H), 4.04 (d, J=9.2 Hz, 2H), 4.41 (dd, J=9.2, 6.0 Hz, 2H), 7.06 (s, 1H), 7.61-7.62 (m, 1H), 8.44 (s, 1H), 8.70 (s, 1H), 8.91 (s, 1H), 12.13 (br, 1H).

Example 14: Synthesis of Compound LW104-B

Preparation of the compound was as described in Example 10 for LW104-A, the material used in this example was 3c, and compound LW104-B was obtained after purification. $^1$HNMR (400 MHz, d6-DMSO): δ 1.23 (t, J=6.4 Hz, 3H), 3.03 (q. J=6.4 Hz, 1H), 3.63 (s, 2H), 4.06 (dd, J=8.0, 4.8 Hz, 2H), 4.16 (s, 1H), 4.43 (d, J=9.2 Hz, 2H), 7.07 (d, J=2.8 Hz, 1H), 7.61 (s, 1H), 8.45 (s, 1H), 8.70 (s, 1H), 8.91 (s, 1H), 12.13 (br, 1H). MS-ESI: [M+Na]$^+$=393.

Example 15: Synthesis of Compound 1d

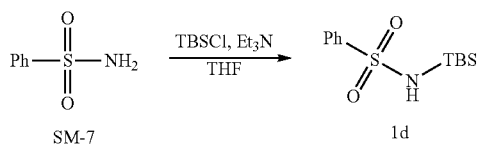

Preparation of the compound was as described in Example 7 for 1b, the material used in this example was SM-7, and compound 1d was obtained after purification.

Example 16: Synthesis of Compound 2d

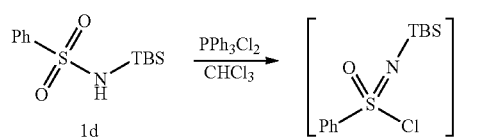

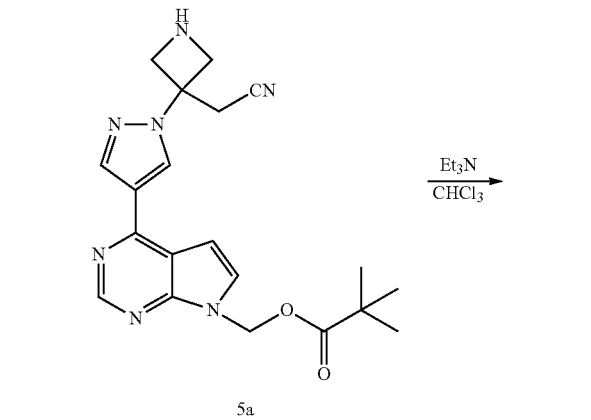

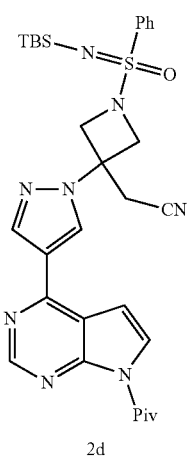

Preparation of the compound was as described in Example 8 for 2b, the material used in this example was 1d, and compound 2d was obtained after purification.

Example 17: Synthesis of Compound 3d

Preparation of the compound was as described in Example 9 for 3b, the material used in this example was 2d, and compound 3d was obtained after purification.

Example 18: Synthesis of Compound LW104-C

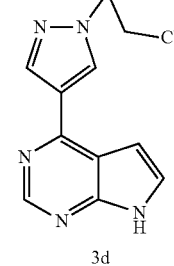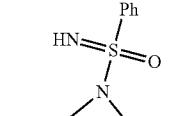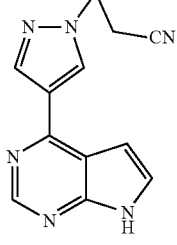

Preparation of the compound was as described in Example 10 for LW104-A, the material used in this example was 3d, and compound LW104-C was obtained after purification. $^1$HNMR (400 MHz, d6-DMSO): δ 3.97 (dd, J=9.6, 4.8 Hz, 2H), 4.21 (t, J=9.6 Hz, 2H), 4.74 (s, 1H), 5.28 (t, J=4.8 Hz, 2H), 6.96 (d, J=1.6 Hz, 1H), 7.20-7.23 (m, 1H), 7.36 (d, J=8.8 Hz, 1H), 7.52-7.53 (m, 3H), 7.57 (t, J=7.2 Hz, 1H), 7.85-7.88 (m, 2H), 8.25 (s, 1H), 8.62 (d, J=8.0 Hz, 1H), 12.09 (br, 1H). MS-ESI: [M–H]$^+$=417.

Example 19: Synthesis of Compound 1e

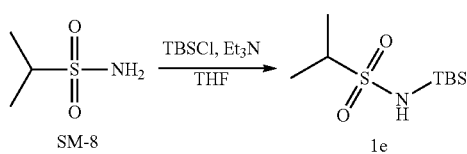

Preparation of the compound was as described in Example 7 for 1b, the material used in this example was SM-8, and compound 1e was obtained after purification. ¹HNMR (400 MHz, CDCl₃): δ 0.22 (s, 6H), 0.88 (s, 9H), 1.30 (s, 3H), 1.32 (s, 3H), 2.99-3.06 (m, 1H), 3.69 (br, 1H)

Example 20: Synthesis of Compound 2e

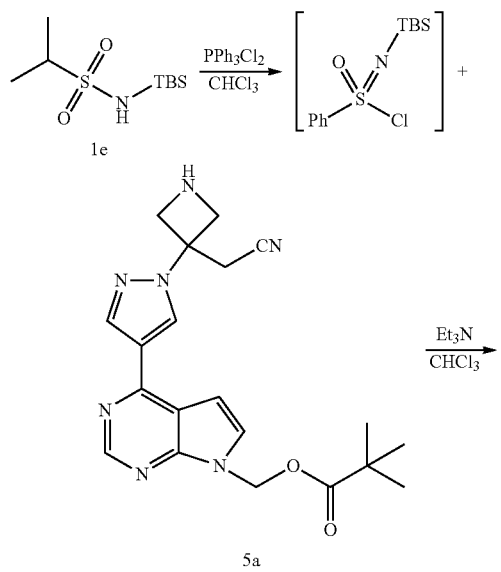

Preparation of the compound was as described in Example 8 for 2b, the material used in this example was 1e, and compound 2e was obtained after purification.

Example 21: Synthesis of Compound 3e

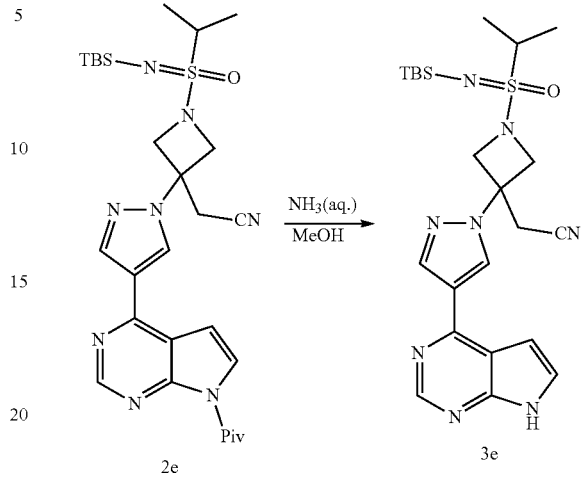

Preparation of the compound was as described in Example 9 for 3b, the material used in this example was 2e, and compound 3e was obtained after purification. ¹HNMR (400 MHz, d6-DMSO): δ 0.01 (s, 3H), 0.03 (s, 3H), 0.82 (s, 9H), 1.26 (m, 6H), 3.09-3.16 (m, 1H), 3.62 (s, 2H), 3.98 (d, J=9.2 Hz, 2H), 4.40 (dd, J=8.8, 5.6 Hz, 2H), 7.05 (d, J=3.6 Hz, 1H), 7.60-7.62 (m, 1H), 8.43 (s, 1H), 8.70 (s, 1H), 8.90 (s, 1H), 12.12 (br, 1H).

Example 22: Synthesis of Compound LW104-D

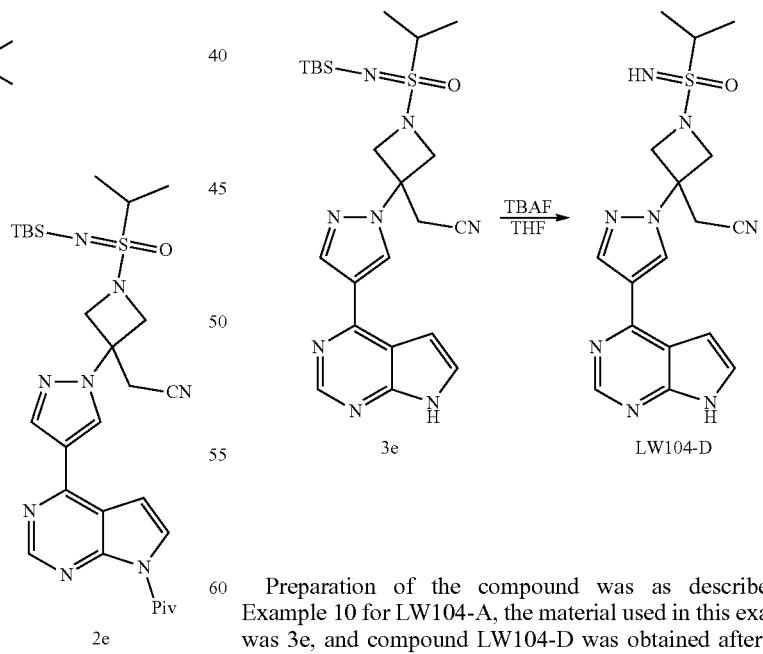

Preparation of the compound was as described in Example 10 for LW104-A, the material used in this example was 3e, and compound LW104-D was obtained after purification. ¹HNMR (400 MHz, d6-DMSO): δ 1.23-1.25 (m, 6H), 3.10-3.20 (m, 1H), 3.64 (s, 2H), 4.02 (dd, J=15.6, 8.4 Hz, 2H), 4.45 (dd, J=15.6, 8.4 Hz, 2H), 7.07 (d, J=2.0 Hz, 1H), 7.60-7.62 (m, 1H), 8.44 (s, 1H), 8.70 (s, 1H), 8.90 (s, 1H), 12.16 (br, 1H). MS-ESI: [M+Na]⁺=407.

Example 23: Synthesis of Compound 1f

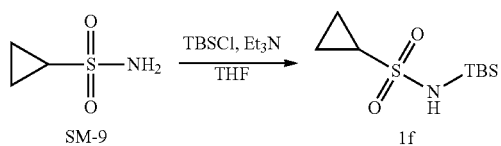

Preparation of the compound was as described in Example 7 for 1b, the material used in this example was SM-9, and compound 1f was obtained after purification. ¹HNMR (400 MHz, CDCl₃): δ 0.28 (s, 6H), 0.93 (s, 9H), 1.13-1.15 (m, 2H), 1.24-1.25 (m, 2H), 2.41-2.47 (m, 1H), 3.94 (br, 1H).

Example 24: Synthesis of Compound 2f

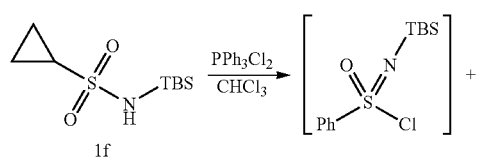

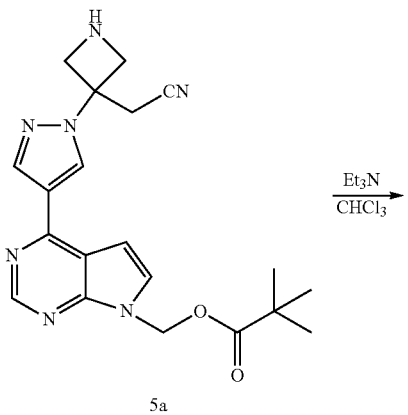

Preparation of the compound was as described in Example 8 for 2b, the material used in this example was 1f, and compound 2f was obtained after purification.

Example 25: Synthesis of Compound 3f

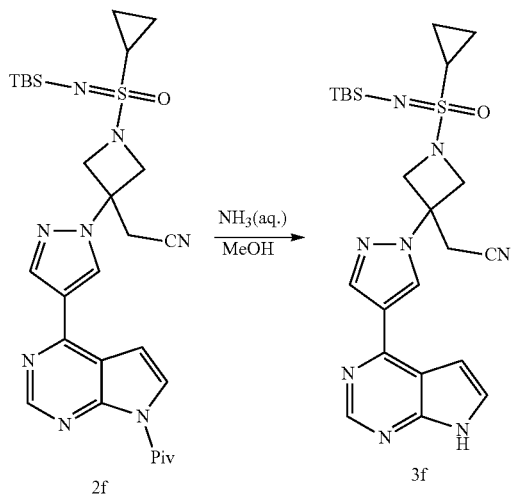

Preparation of the compound was as described in Example 9 for 3b, the material used in this example was 2f, and compound 3f was obtained after purification.

Example 26: Synthesis of Compound LW104-E

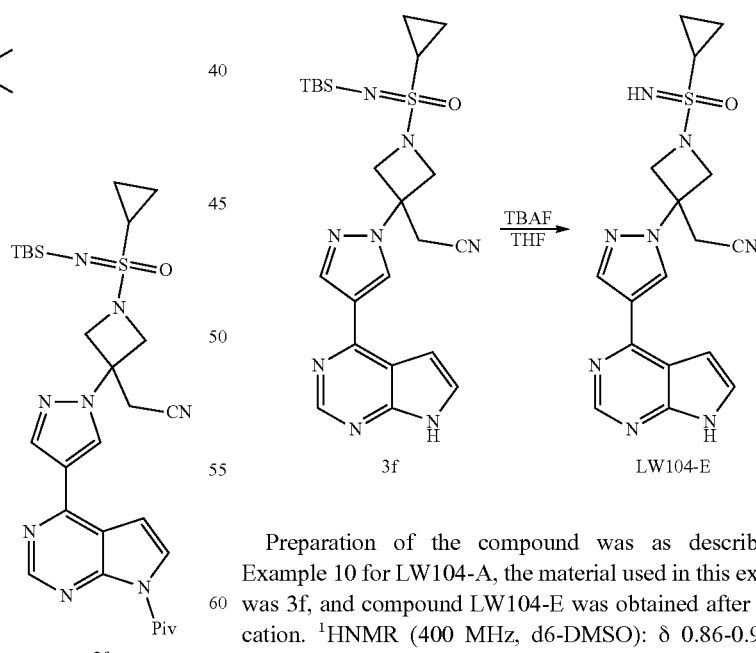

Preparation of the compound was as described in Example 10 for LW104-A, the material used in this example was 3f, and compound LW104-E was obtained after purification. ¹HNMR (400 MHz, d6-DMSO): δ 0.86-0.91 (m, 2H), 1.10-1.15 (m, 2H), 2.58-2.61 (m, 1H), 3.59 (s, 2H), 4.02 (s, 2H), 4.09 (s, J=9.6 Hz, 2H), 4.46 (dd, J=9.2, 1.6 Hz, 2H), 7.04 (d, J=2.0 Hz, 1H), 7.58 (d, J=3.2 Hz, 1H), 8.42 (s, 1H), 8.67 (s, 1H), 8.89 (s, 1H), 12.10 (br, 1H). MS-ESI: [M+H]⁺=383.

Example 27: Synthesis of Compound 1g

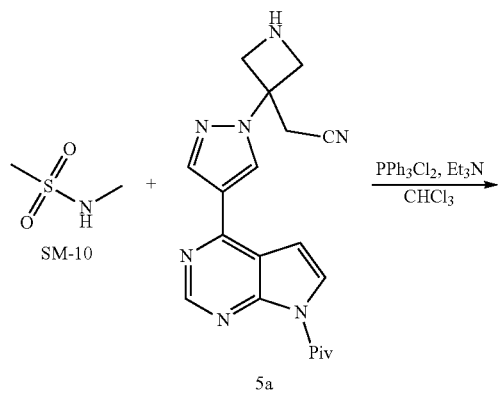

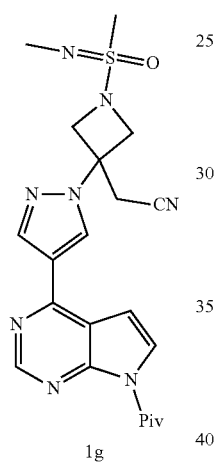

Under the protection of nitrogen, 0.36M Ph₃PCl₂/chloroform suspension (9.7 ml, 3.5 mmol) was cooled to 0° C., and triethylamine (482 mg, 4.77 mmol) was added, and the mixture was stirred for 15 min. SM-10 (500 mg, 3.0 mmol) was added at 0° C. After the mixture was stirred for 20 min, the compound 5a (200 mg, 0.53 mmol) was added to the above reaction system, and the reaction was warmed to room temperature and stirred overnight. TLC showed that some of the starting material has not been consumed. The reaction was quenched by being added with water, and extracted with ethyl acetate. Organic phase was concentrated and column chromatography isolated, eluent (n-heptane/ethyl acetate=1:1, and followed by CH₂Cl₂/MeOH=30/1), to provide white solid 1g (150 mg). ¹HNMR (400 MHz, d6-DMSO): δ 1.09 (s, 9H), 2.55 (s, 3H), 3.01 (s, 3H), 3.67 (s, 2H), 4.16 (dd, J=8.8, 2.0 Hz, 2H), 4.53 (dd, J=13.6, 9.6 Hz, 2H), 6.25 (s, 2H), 7.21 (d, J=4.0 Hz, 1H), 7.76 (d, J=4.4 Hz, 1H), 8.50 (s, 1H), 8.82 (s, 1H), 8.96 (s, 1H).

Example 28: Synthesis of Compound LW104-F

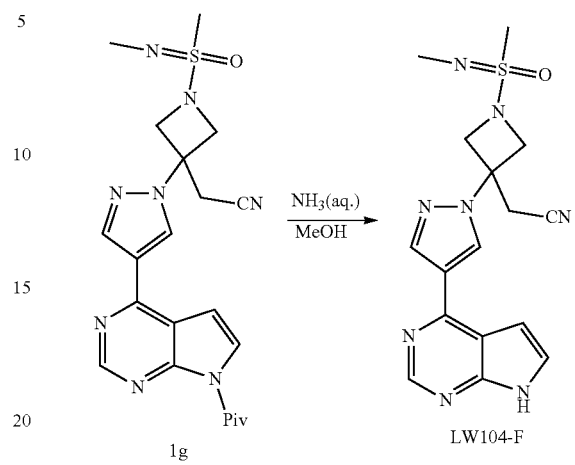

The compound 2b (140 mg) was dissolved in methanol (5 ml), and ammonia water (3 ml) was added at room temperature. Some raw materials were precipitated, and the solid gradually dissolved as the reaction progressed. After reacted for 18 h, TLC showed that the starting material was consumed. The reaction solution was extracted by EA, dried and concentrated, column chromatography isolated (dichloromethane/methanol=15/1) to provide a white solid. LW104-F (600 mg). ¹HNMR (400 MHz, d6-DMSO): δ 2.56 (s, 3H), 3.00 (s, 3H), 3.67 (s, 2H), 4.16 (d, J=9.2 Hz, 2H), 4.53 (dd, J=14.8, 9.2 Hz, 2H), 7.08 (d, J=2.8 Hz, 1H), 7.61-7.62 (m, 1H), 8.47 (s, 1H), 8.71 (s, 1H), 8.92 (s, 1H), 12.03 (br, 1H). MS-ESI: [M+Na]⁺=393.

Example 29: Synthesis of Compound 1h

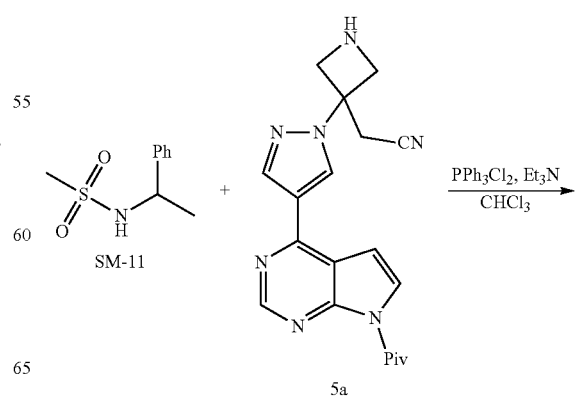

-continued

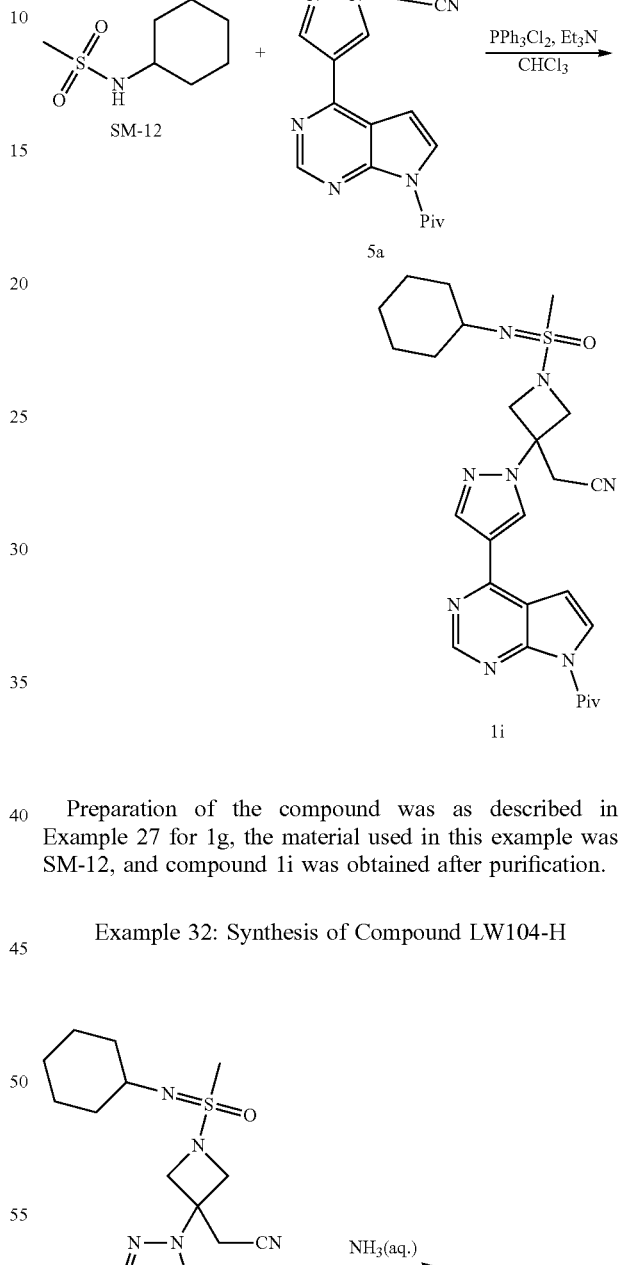

1h

Preparation of the compound was as described in Example 27 for 1g, the material used in this example was SM-11, and compound 1h was obtained after purification.

Example 30: Synthesis of Compound LW104-G

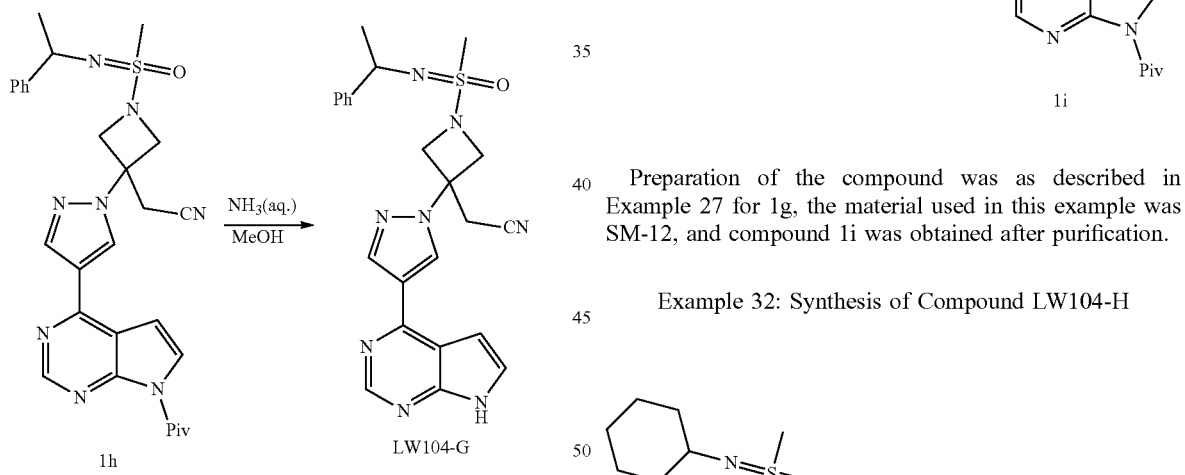

1h → LW104-G

Preparation of the compound was as described in Example 28 for LW104-F, the material used in this example was 1 h, and compound LW104-G was obtained after purification. $^1$HNMR (400 MHz, d6-DMSO): δ 1.29-1.33 (m, 3H), 3.04 (s, 3H), 3.49 (d, J=12.8 Hz, 2H), 3.58 (d, J=9.2 Hz, 1H), 4.00 (d, J=8.8 Hz, 1H), 4.14 (d, J=8.8 Hz, 1H), 4.38 (d, J=9.2 Hz, 1H), 4.57 (q, J=6.8 Hz, 1H), 7.05 (d, J=2.4 Hz, 1H), 7.16-7.17 (m, 1H), 7.24-7.28 (m, 2H), 7.35-7.36 (m, 2H), 7.60-7.62 (m, 1H), 8.41 (s, 1H), 8.70 (s, 1H), 8.77 (s, 1H), 12.14 (br, 1H). MS-ESI: [M–H]$^+$=459.

Example 31: Synthesis of Compound 1i

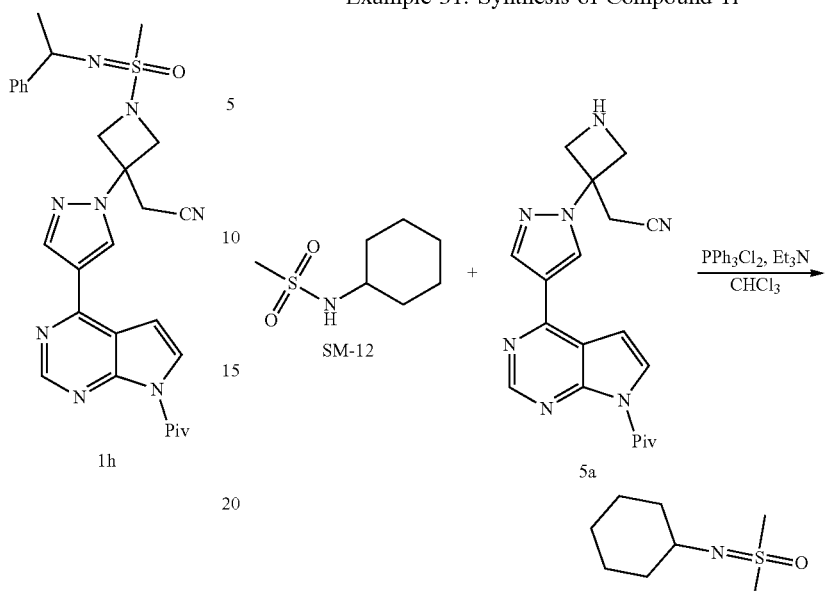

Preparation of the compound was as described in Example 27 for 1g, the material used in this example was SM-12, and compound 1i was obtained after purification.

Example 32: Synthesis of Compound LW104-H

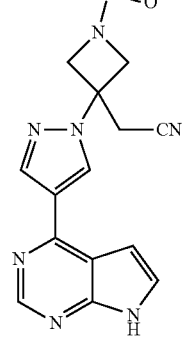

LW104-H

Preparation of the compound was as described in Example 28 for LW104-F, the material used in this example was 1i, and compound LW104-H was obtained after purification. ¹HNMR (400 MHz, d6-DMSO): δ 1.29-1.33 (m, 3H), 3.04 (s, 3H), 3.49 (d, J=12.8 Hz, 2H), 3.58 (d, J=9.2 Hz, 1H), 4.00 (d, J=8.8 Hz, 1H), 4.14 (d, J=8.8 Hz, 1H), 4.38 (d, J=9.2 Hz, 1H), 4.57 (q, J=6.8 Hz, 1H), 7.05 (d, J=2.4 Hz, 1H), 7.16-7.17 (m, 1H), 7.24-7.28 (m, 2H), 7.35-7.36 (m, 2H), 7.60-7.62 (m, 1H), 8.41 (s, 1H), 8.70 (s, 1H), 8.77 (s, 1H), 12.14 (br, 1H). MS-ESI: [M−H]⁺=459.

Example 33: Synthesis of Compound 1j

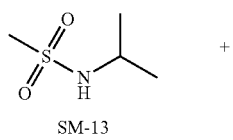

SM-13

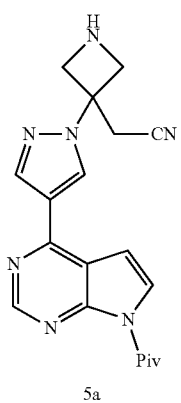

5a

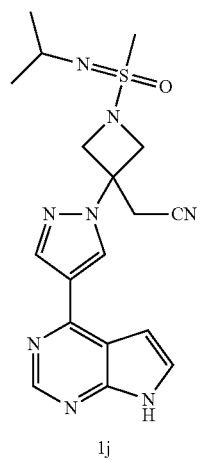

1j

Preparation of the compound was as described in Example 27 for 1g, the material used in this example was SM-13, and compound 1j was obtained after purification.

Example 34: Synthesis of Compound LW104-I

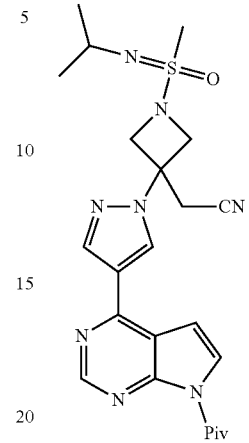

1j

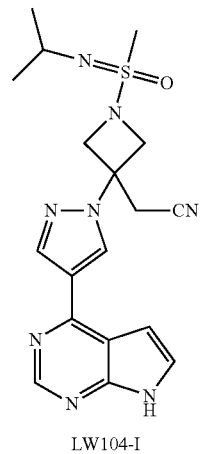

LW104-I

Preparation of the compound was as described in Example 28 for LW104-F, the material used in this example was 1j, and compound LW104-I was obtained after purification. ¹HNMR (400 MHz, d6-DMSO): δ 1.07-1.29 (m, 6H), 1.61-1.70 (m, 4H), 2.98 (s, 3H), 3.18-3.23 (m, 1H), 3.65 (s, 2H), 4.14 (t, J=8.4 Hz, 2H), 4.51 (dd, J=9.2, 6.0 Hz, 2H), 7.09 (dd, J=3.2, 0.8 Hz, 1H), 7.61 (t, J=2.8 Hz, 1H), 8.47 (s, 1H), 8.70 (s, 1H), 8.91 (s, 1H), 12.14 (br, 1H), MS-ESI: [M−H]⁺=437.

Example 35: Synthesis of Compound LW104-J

LW104-J was from the first peak prepared by chiral resolution of compound LW104-B. The preparation method: Column: Chiralpak IA; Flow Rate: 1.0 mL/min: Mobile Phase: Methanol/Acetonitrile=90/10; Wavelength: 24 nm; Column Temperature: 35° C. ¹HNMR (400 MHz, d6-DMSO): δ 1.23 (t, J=6.4 Hz, 3H), 3.03 (q, J=6.4 Hz, 1H), 3.63 (s, 2H), 4.06 (dd, J=8.0, 4.8 Hz, 2H), 4.16 (s, 1H), 4.44 (d, J=9.2 Hz, 2H), 7.08 (d, J=2.8 Hz, 1H), 7.62 (s, 1H), 8.46 (s, 1H), 8.71 (s, 1H), 8.92 (s, 1H), 12.14 (br, 1H). MS-ESI: [M+Na]⁺=393

Example 36: Synthesis of Compound LW104-K

LW104-K was from the second peak prepared by chiral resolution of compound LW104-B. The preparation method: Column: Chiralpak IA; Flow Rate: 1.0 mL/min: Mobile Phase: Methanol/Acetonitrile=90/10; Wavelength: 24 nm; Column Temperature: 35° C. ¹HNMR (400 MHz, d6-DMSO): δ 1.23 (t, J=6.4 Hz, 3H), 3.04 (q, J=6.4 Hz, 1H), 3.63 (s, 2H), 4.06 (dd, J=8.0, 4.8 Hz, 2H), 4.16 (s, 1H), 4.45 (d, J=9.2 Hz, 2H), 7.08 (d, J=2.8 Hz, 1H), 7.61 (s, 1H), 8.45 (s, 1H), 8.71 (s, 1H), 8.91 (s, 1H), 12.13 (br, 1H). MS-ESI: [M+Na]⁺=393.

Example 37: Synthesis of Compound 1k

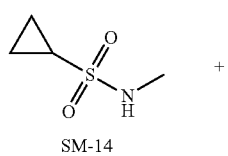

SM-14

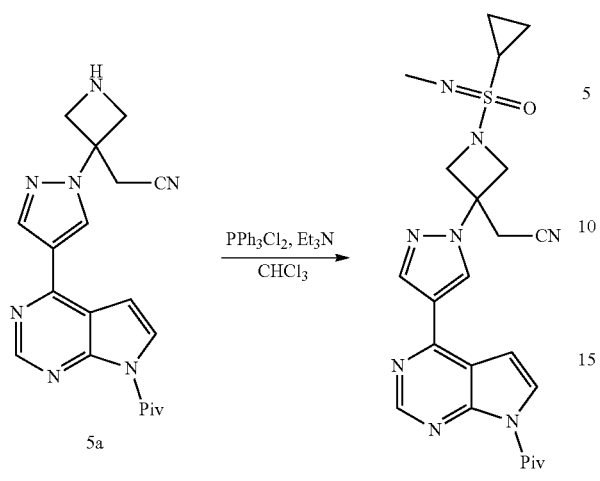

Preparation of the compound was as described in Example 27 for 1g, the material used in this example was SM-14, and compound 1k was obtained after purification. ¹H NMR (400 MHz, DMSO-$d_6$) δ 8.98 (s, 1H), 8.80 (s, 1H), 8.51 (s, 1H), 7.81 (d, J=3.7 Hz, 1H), 7.21 (d, J=3.7 Hz, 1H), 5.65 (s, 2H), 4.62 (dd, J=9.2, 3.0 Hz, 2H), 4.22 (dd, J=9.2, 2.6 Hz, 2H), 3.69 (s, 2H), 3.54 (t, J=8.0 Hz, 2H), 2.78 (tt, J=7.6, 5.1 Hz, 1H), 2.60 (s, 3H), 1.07-1.01 (m, 1H), 0.98-0.88 (m, 3H), 0.84 (t, J=8.0 Hz, 2H), −0.10 (s, 9H).

Example 38: Synthesis of Compound LW104-L

Example 39: Synthesis of Compound 11

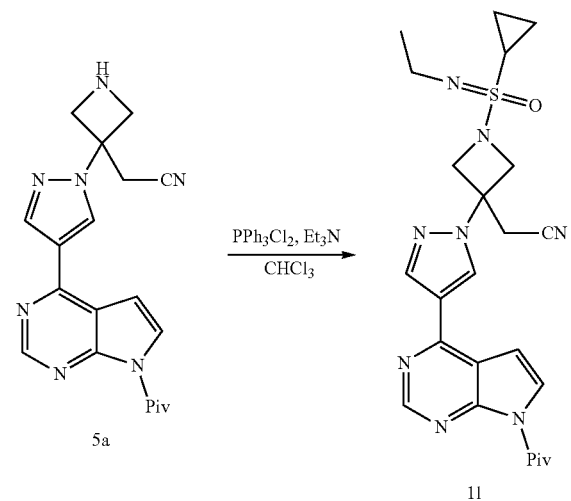

Preparation of the compound was as described in Example 27 for 1g, the material used in this example was SM-15, and compound 11 was obtained after purification. MS-ESI: [M+H]⁺=541.

Example 38: Synthesis of Compound LW104-M

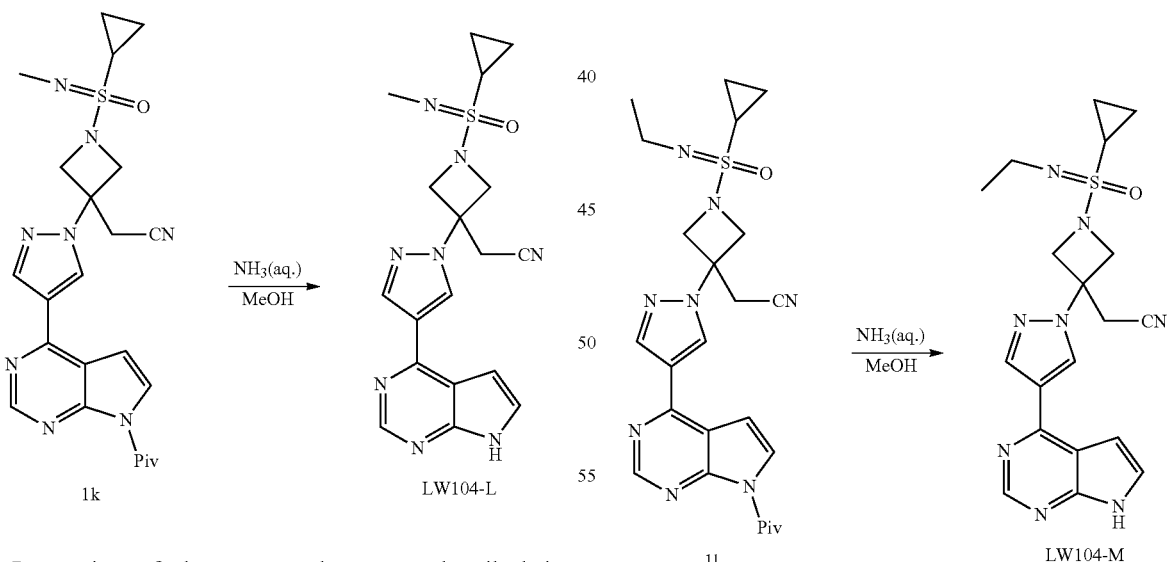

Preparation of the compound was as described in Example 28 for LW104-F, the material used in this example was 1k, and compound LW104-L was obtained after purification. ¹H NMR (400 MHz, DMSO-$d_6$) δ 12.15 (s, 1H), 8.94 (s, 1H), 8.71 (s, 1H), 8.47 (s, 1H), 7.62 (dd, J=3.5, 2.3 Hz, 1H), 7.09 (dd, J=3.6, 1.7 Hz, 1H), 4.60 (dd, J=9.2, 4.5 Hz, 2H), 4.19 (dd, J=9.1, 2.3 Hz; 2H), 3.67 (s, 2H), 2.77 (m, J=12.7, 6.3, 5.8 Hz; 1H), 2.59 (s, 3H), 1.06-0.99 (m, 1H), 0.96-0.87 (m, 3H). MS-ESI: [M+H]⁺=397.

Preparation of the compound was as described in Example 28 for LW104-F, the material used in this example was II, and compound LW104-M was obtained after purification. ¹H NMR (400 MHz, DMSO-$d_6$) δ 12.14 (s, 1H), 8.93 (s, 1H), 8.71 (s, 1H), 8.47 (s, 1H), 7.62 (dd, J=3.6, 2.4 Hz, 1H), 7.09 (dd, J=3.6, 1.7 Hz, 1H), 4.59 (dd, J=9.2, 3.7 Hz, 2H), 4.18 (dd, J=9.1, 4.6 Hz, 2H), 3.66 (s, 2H), 2.99 (q, J=7.1 Hz, 2H), 2.81-2.71 (m, 1H), 1.04 (t, J=7.2 Hz, 3H), 0.92 (m, 4H). MS-ESI: [M+Na]$^+$=411.

Example 39: Synthesis of Compound 1m

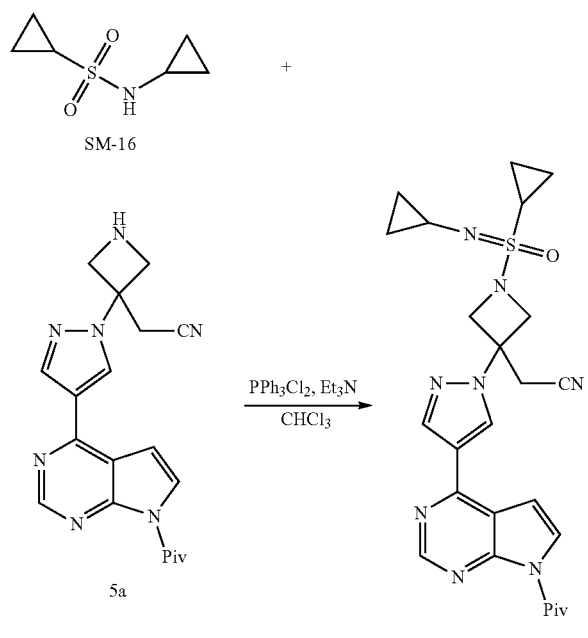

Preparation of the compound was as described in Example 27 for 1g, the material used in this example was SM-16, and compound 1m was obtained after purification. MS-ESI: [M+H]$^+$=553.

Example 40: Synthesis of Compound LW104-N

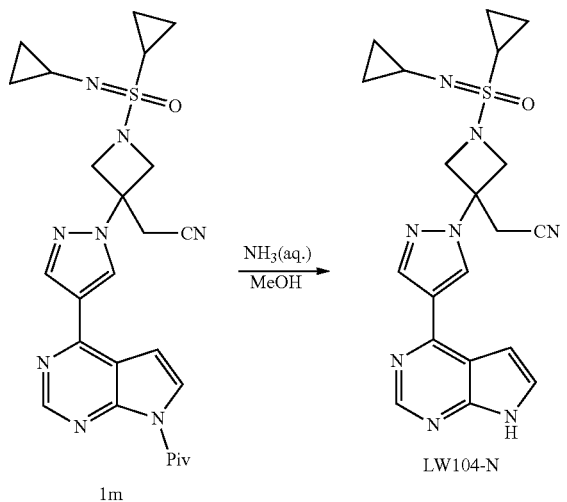

Preparation of the compound was as described in Example 28 for LW104-F, the material used in this example was 1m, and compound LW104-N was obtained after purification. $^1$H NMR (400 MHz, DMSO-d$_6$) δ 12.14 (s, 1H), 8.95 (s, 1H), 8.71 (s, 1H), 8.47 (s, 1H), 7.62 (dd, J=3.6, 1.7 Hz, 1H), 7.09 (dd, J=3.4, 1.5 Hz, 1H), 4.62 (d, J=8.8 Hz, 2H), 4.23 (dd, J=9.2, 4.9 Hz, 2H), 3.66 (s, 2H), 2.74 (m, 1H), 2.53 (d, J=4.3 Hz, 1H), 1.07-0.97 (m, 1H), 0.96-0.84 (m, 3H), 0.48-0.37 (m, 2H), 0.35-0.22 (m, 2H). MS-ESI: [M+H]$^+$=423.

Example 41: Synthesis of Compound 1n

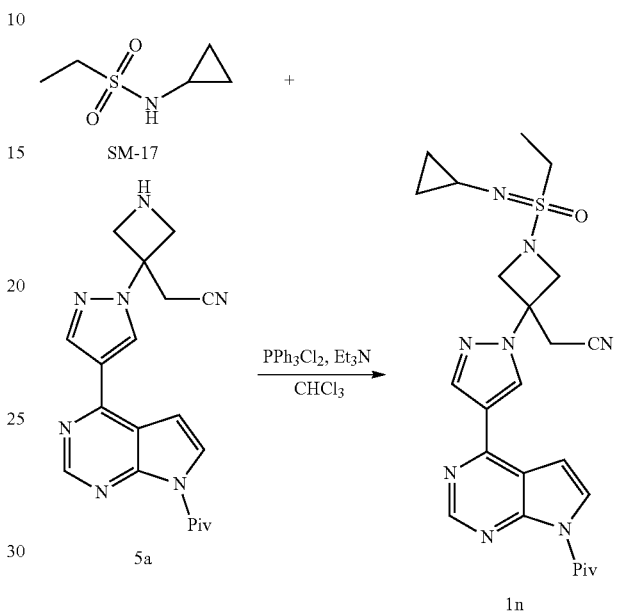

Preparation of the compound was as described in example 27 for 1g, the material used in this example was SM-17, and compound 1n was obtained after purification. $^1$H NMR (400 MHz, DMSO-d6) δ 8.98 (s, 1H), 8.80 (s, 1H), 8.51 (s, 1H), 7.79 (d, J=3.7 Hz, 1H), 7.21 (d, J=3.7 Hz, 1H), 5.65 (s, 2H), 4.63 (dd, J=8.9, 6.4 Hz, 2H), 4.23 (dd, J=9.0, 2.7 Hz, 2H), 3.70 (s, 2H), 3.54 (t, J=8.0 Hz, 2H), 3.16 (q, J=7.2 Hz, 2H), 2.56 (tt, J=7.1, 3.8 Hz, 1H), 1.22 (t, J=7.3 Hz, 3H), 0.83 (t, J=8.0 Hz, 2H), 0.51-0.19 (m, 4H), −0.11 (s, 9H).

Example 42: Synthesis of Compound LW104-O

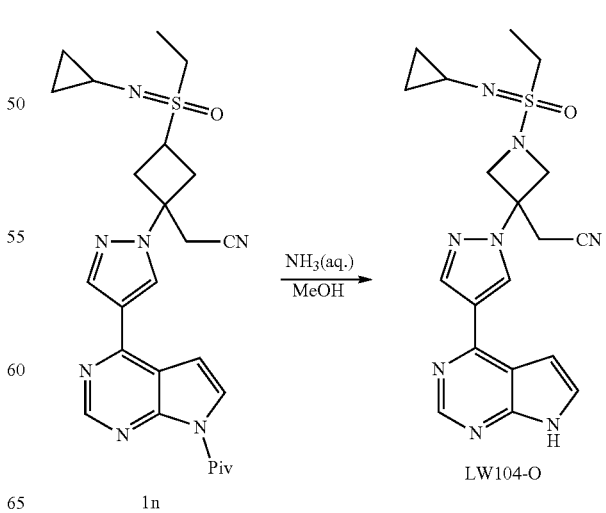

Preparation of the compound was as described in Example 28 for LW104-F, the material used in this example was 1n, and compound LW104-O was obtained after purification. $^1$H NMR (400) MHz; DMSO-d6) δ 12.16 (s, 1H), 8.94 (s, 1H), 8.71 (s, 1H), 8.48 (s, 1H), 7.83-7.44 (m, 1H), 7.10 (dd, J=3.4, 1.5 Hz, 1H), 4.59 (dd, J=9.1, 2.7 Hz, 2H), 4.19 (dd, J=9.1, 3.1 Hz, 2H), 3.68 (s, 2H), 3.15 (q, J=7.2 Hz, 2H), 2.55 (dd, J=7.1, 3.7 Hz, 1H), 1.21 (t, J=7.3 Hz, 3H), 0.57-0.13 (m, 4H). MS-ESI: [M+H]$^+$=411.

Test Example: Detecting JAK1-3 Enzyme Activity Inhibitory Effect of Compounds

Reagents and Consumables

JAK1 (Invitrogen, Cat. No PV4775), JAK2 (Invitrogen, Cat. No PV4288), JAK3 (Invitrogen, Cat. No PV4080), ATP (Sigma. Cat. No. A7699-1G), DMSO (Sigma, Cat. No. D2650), DTT (Sigma, Cat. No. 43815).

384-well plate compound dilution plate (Greiner, Cat. No. 781280), 384-well plate test plate (Perkin Elmer, Cat. No. 6007299), LANCE Ultra ULight™-JAK-1 peptide (Perkin Elmer, Cat. No. TRF0121), LANCE Eu-W1024 Anti-phosphotyrosine (PT66) (Perkin Elmer, Cat. No. AD0069), LANCE™ Detection Buffer (Perkin Elmer, Cat. No. CR97-100).

Experimental Method

Final Test Concentration of Compounds:

The final test concentration of the test compounds was from 10M to 0.17 nM, 3-fold gradient diluted, at 11 concentrations.

The final test concentration of reference compound Tofacitinib was from 1M to 0.017 nM, 3-fold gradient diluted, at 11 concentrations.

Kinase Assay:

Preparation of buffers, the buffer included 50 mM HEPES (pH 7.5), 0.01% Brij-35, 10 mM MgCl$_2$, and 1 mM EGTA.

After the buffer was formulated, the enzyme and substrate were mixed with different concentrations of the compound prepared in advance, and placed at room temperature for 15 minutes. ATP was added to start reaction, and the reaction solution was incubated at room temperature for 90 minutes (positive and negative controls were set). 10 µL of reaction system included 2.5 µL compound, 5 µL mixture of enzyme and substrate, and 2.5 µL ATP. After the reaction was completed, the antibody was added to test and incubated at room temperature for 60 min, then was detected by Evnvision and data was collected. Data analysis and mapping was conducted with XLfit5 software.

The test results of JAK1-3 enzyme inhibitory activity and cytostatic activity of the compounds of the present invention are shown in Table 1.

TABLE 1

JAK activity inhibition result of compounds of the present invention

| No. | Compound | JAK1 inhibitory activity IC$_{50}$ (nM) | JAK2 inhibitory activity IC$_{50}$ (nM) | JAK3 inhibitory activity IC$_{50}$ (nM) | JAK3/ JAK1 | JAK3/ JAK2 |
|---|---|---|---|---|---|---|
| 1 | LW104-A | A | A | 98.3 | 18.4 | 22.1 |
| 2 | LW104-B | A | A | 136 | 37.3 | 23.5 |
| 3 | LW104-C | B | B | 427 | 19.9 | 27.9 |
| 4 | LW104-D | A | A | 190 | 43.2 | 26.6 |
| 5 | LW104-E | A | A | 187 | 40.7 | 30.6 |
| 6 | LW104-F | A | A | 145 | 30.7 | 23.2 |
| 7 | LW104-G | B | B | 158.1 | 35.9 | 18.5 |
| 8 | LW104-I | B | B | 649 | 36.9 | 17.0 |
| 9 | LW104-J | A | A | 116 | 32.1 | 34.6 |
| 10 | LW104-K | A | A | 69.3 | 27.3 | 26.6 |
| 11 | LW104-L | A | A | 158 | 40.3 | 35.0 |
| 12 | LW104-M | A | A | 194 | 30.2 | 23.9 |
| 13 | LW104-N | A | A | 203 | 29.0 | 24.2 |
| 14 | LW104-O | A | B | 294 | 47.4 | 23.9 |
| 15 | LW104-P | A | B | 216 | 34.6 | 21.2 |
| 16 | Toficitinib | A | A | 0.72 | 0.4 | 0.2 |

Wherein the IC$_{50}$ activity is classified according to the following table:

| Inhibitory Activity IC$_{50}$ (nM) | JAK1 | JAK2 |
|---|---|---|
| 0.1-10 | A | A |
| 10-100 | B | B |
| 100-500 | C | C |
| 500-2000 | D | D |

Discussion:

The above experimental results suggest:

(1) the Formula I compounds of the invention exhibit excellent inhibition activity to JAK1 and/or JAK2. The IC$_{50}$ values of the compound of the invention are essentially at 10 nM level or lower, which means that for a subject (such as a patient, especially a rheumatoid arthritis or psoriasis patient) whose body weight is about 70 kg, JAK1 and/or JAK2 can be efficiently suppressed when the daily dose is 10 mg-30 mg.

(2) The compounds of formula I of the present invention exhibit excellent JAK selectivity, i.e., the IC$_{50}$ ratio of JAK3/JAK1 and/or the IC$_{50}$ ratio of JAK3/JAK2 is much superior to currently marketed drugs (e.g., Toficitinib). Unexpectedly, for the compounds of the present invention, the selectivity represented by the IC$_{50}$ ratio of JAK3/JAK1 is increased by about 80 times (32/0.4=80), and the selectivity of preferred compounds improved by ≥100 times: the selectivity represented by ratio of JAK3/JAK2 is increased by approximately 115 times (24.4/0.21=115). Therefore, the side effects of the compounds of the present invention associated with inhibition to JAK3 will be significantly reduced, and the safety will be significantly improved, especially in the case where the daily dose is 10 mg-50 mg. The side effects associated with JAK3 inhibition include (but are not limited to): side effects such as bacterial infection, fungal infection, viral infection, anemia, etc.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of the formula I, or a stereoisomer thereof, a tautomer thereof, or a pharmaceutically acceptable salt, hydrate or solvate thereof:

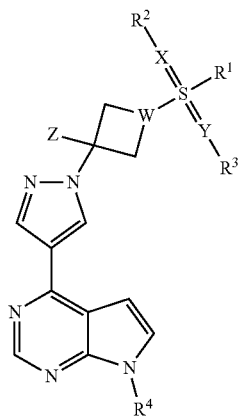

I wherein:
X is $NR^2$ or O;
Y is $NR^3$ or O;
Z is selected from the group consisting of: substituted or unsubstituted C1-C8 alkyl;
W is N;
$R^1$, $R^2$ and $R^3$ are each independently selected from the group consisting of hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_6$-$C_{10}$ aryl, substituted or unsubstituted 5-10 membered heteroaryl with 1-3 heteroatoms selected from N, O and S, substituted or unsubstituted benzo 5-10 membered heteroaryl;
$R^4$ is selected from the group consisting of: hydrogen, substituted or unsubstituted $C_1$-$C_6$ alkyl, substituted or unsubstituted $C_3$-$C_8$ cycloalkyl, substituted or unsubstituted 3-10 membered heterocycloalkyl with 1-3 heteroatoms selected from N, S and O, $CH_2OR^5$, wherein $R^5$ is selected from the group consisting of: $C_1$-$C_6$ alkylcarbonyl and trialkylsilyl;
in the $R^1$, $R^2$, $R^3$, $R^4$ and Z, said substitution is substitution by one or more substituents selected from the group consisting of: halogen, nitro, CN, $C_1$-$C_6$ alkyl, halogenated $C_1$-$C_6$ alkyl, and $C_1$-$C_6$ alkoxy.

2. The compound of claim 1, or a stereoisomer thereof, a tautomer thereof, or a pharmaceutically acceptable salt, hydrate or solvate thereof, wherein when X and Y are different, the compound of formula I is a compound of formula II or formula III:

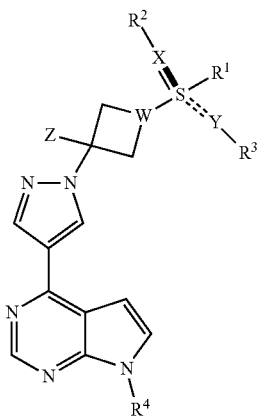

II

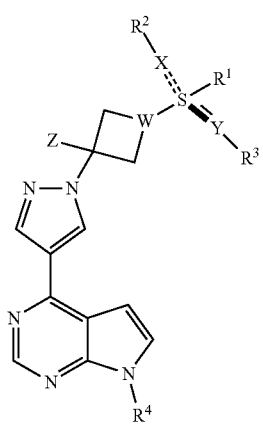

III

3. The compound of claim 1, or a stereoisomer thereof, a tautomer thereof, or a pharmaceutically acceptable salt, hydrate or solvate thereof, wherein the compound of formula I is a compound of formula IV:

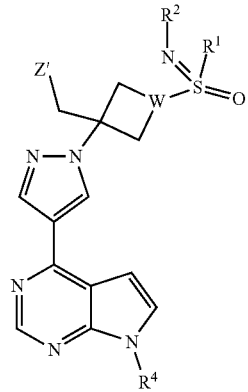

IV in the formula IV, Z' is selected from the group consisting of halogen, nitrile, nitro, and $C_1$-$C_6$ alkyl.

4. The compound of claim 1, or a stereoisomer thereof, a tautomer thereof, or a pharmaceutically acceptable salt, hydrate or solvate thereof, wherein the formula I compound is selected from the group consisting of:

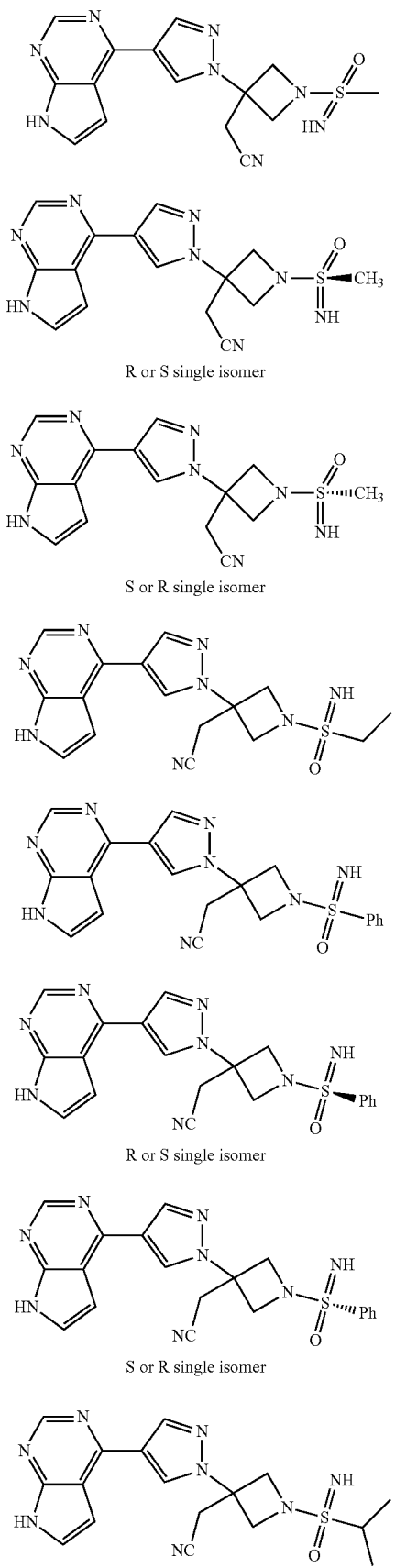
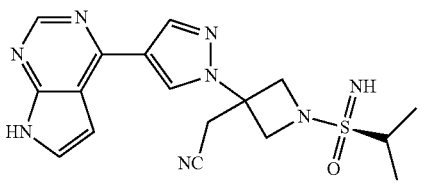
LW104-D-1
R or S single isomer
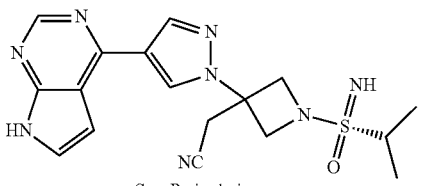
LW104-D-2
S or R single isomer
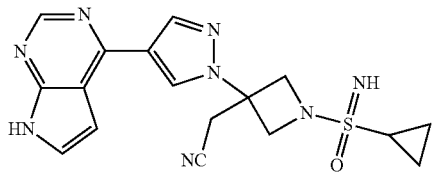
LW104-E
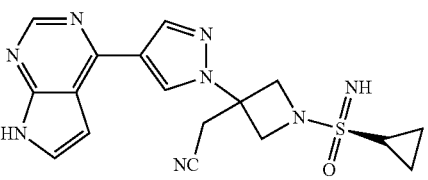
LW104-E-1
R or S single isomer
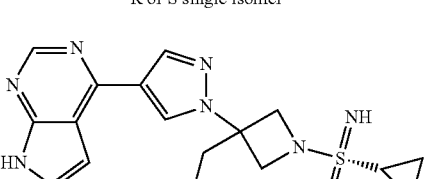
LW104-E-2
S or R single isomer
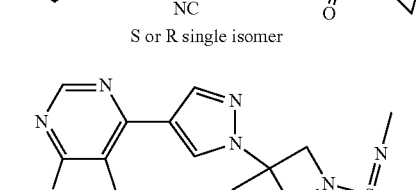
LW104-F
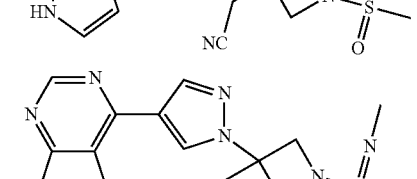
LW104-F-1
R or S single isomer
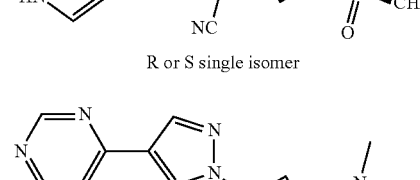
LW104-F-2
S or R single isomer

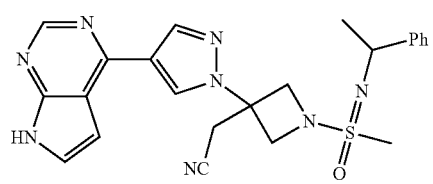
LW104-G
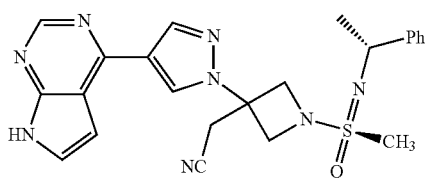
LW104-G-1
R or S single isomer
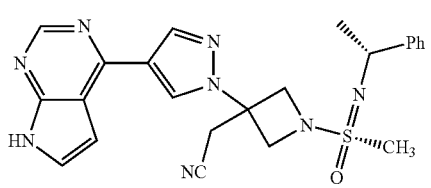
LW104-G-2
S or R single isomer
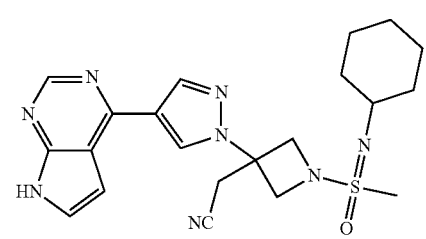
LW104-H
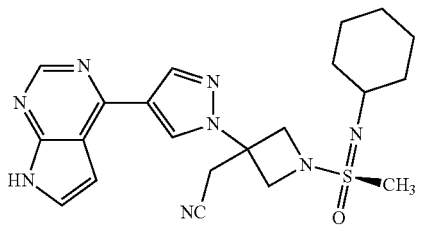
LW104-H-1
R or S single isomer
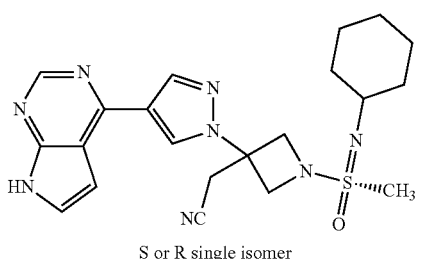
LW104-H-2
S or R single isomer
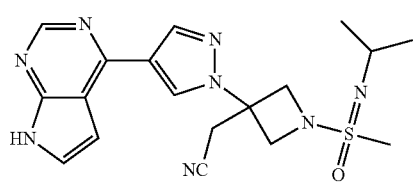
LW104-I
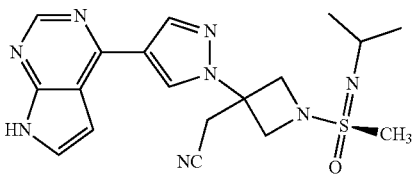
LW104-I-1
R or S single isomer
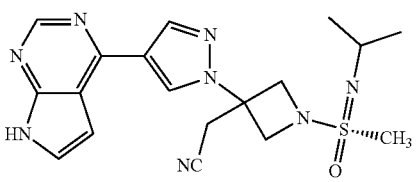
LW104-I-2
S or R single isomer
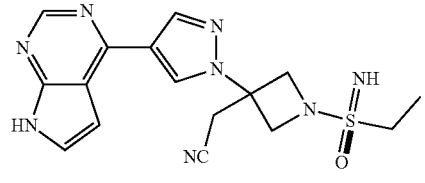
LW104-J
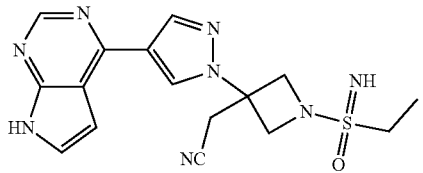
LW104-K
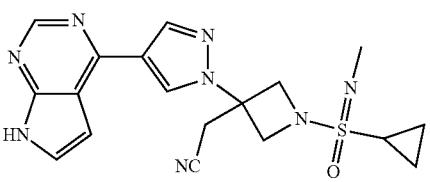
LW104-L
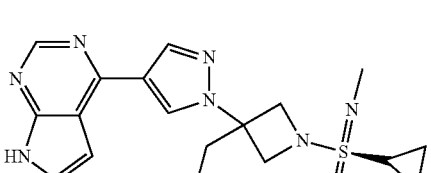
LW104-L-1
R or S single isomer
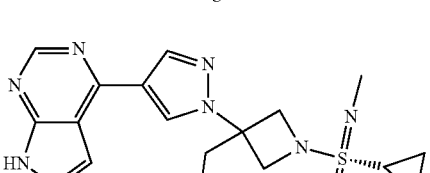
LW104-L-2
S or R single isomer
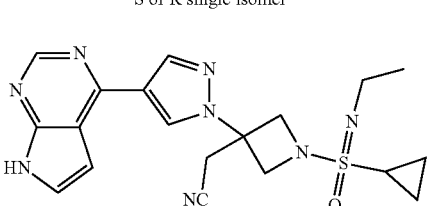
LW104-M

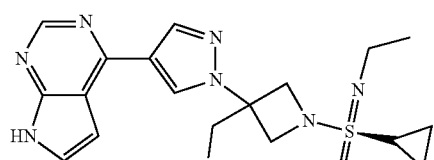
LW104-M-1
R or S single isomer

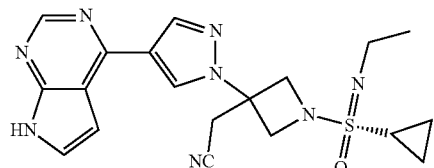
LW104-M-2
S or R single isomer

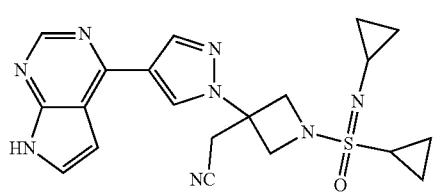
LW104-N

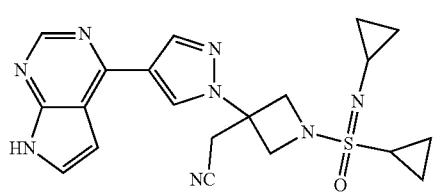
LW104-N-1
R or S single isomer

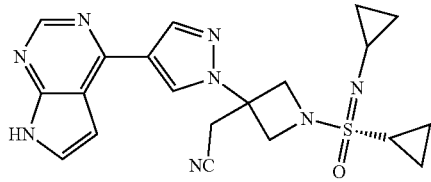
LW104-N-2
S or R single isomer

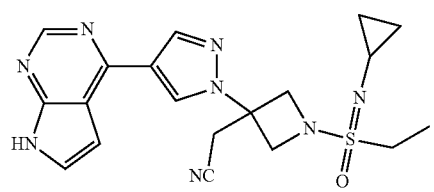
LW104-O

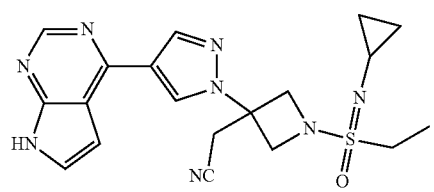
LW104-O-1
R or S single isomer

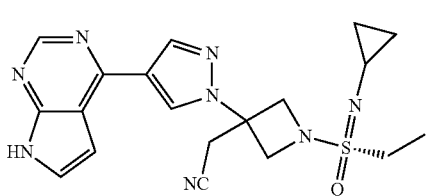
LW104-O-2
S or R single isomer

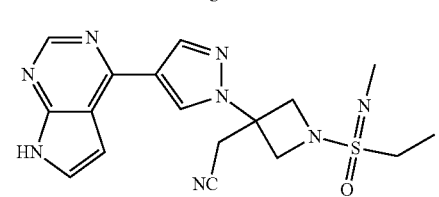
LW104-P

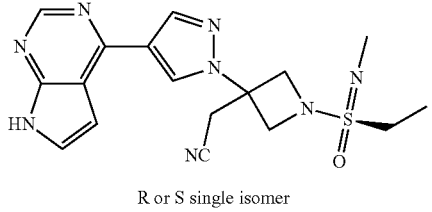
LW104-P-1
R or S single isomer

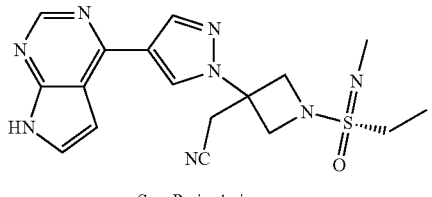
LW104-P-2
S or R single isomer

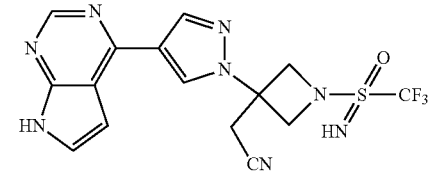
LW104-Q

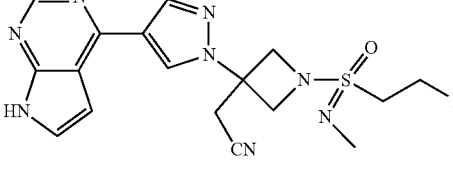
LW104-R

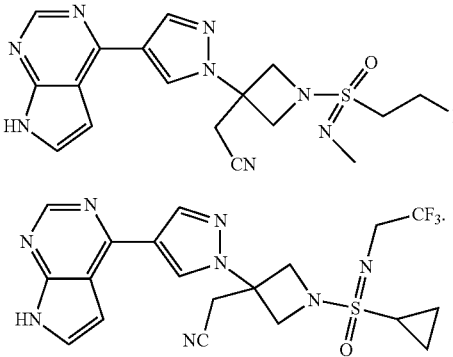
LW104-S

5. A pharmaceutical composition, which comprises (1) the compound of claim 1, or the stereoisomer thereof, tautomer thereof, or a pharmaceutically acceptable salt, hydrate or solvate thereof, and (2) pharmaceutically acceptable carriers.

* * * * *